United States Patent
Sison et al.

(10) Patent No.: US 12,023,508 B2
(45) Date of Patent: Jul. 2, 2024

(54) IMPLANT TO IMPLANT COMMUNICATION FOR USE WITH IMPLANTABLE MEDICAL DEVICES

(71) Applicant: Pacesetter, Inc., Sylmar, CA (US)

(72) Inventors: Shiloh Sison, Alameda, CA (US); Xi Lin Chen, Stevenson Ranch, CA (US); Xiyao Xin, Northridge, CA (US); Xin Huang, Fremont, CA (US)

(73) Assignee: Pacesetter, Inc., Sylmar, CA (US)

( * ) Notice: Subject to any disclaimer, the term of this patent is extended or adjusted under 35 U.S.C. 154(b) by 166 days.

(21) Appl. No.: 17/684,969

(22) Filed: Mar. 2, 2022

(65) Prior Publication Data

US 2022/0370810 A1 Nov. 24, 2022

Related U.S. Application Data

(60) Provisional application No. 63/191,854, filed on May 21, 2021.

(51) Int. Cl.
*A61N 1/372* (2006.01)
*A61N 1/375* (2006.01)
(Continued)

(52) U.S. Cl.
CPC ..... *A61N 1/37282* (2013.01); *A61N 1/37217* (2013.01); *A61N 1/3756* (2013.01); *A61N 1/3787* (2013.01); *A61N 1/3956* (2013.01)

(58) Field of Classification Search
CPC ........................ A61N 1/37282; A61N 1/37217
(Continued)

(56) References Cited

U.S. PATENT DOCUMENTS

| 8,606,365 B2 | 12/2013 | Sison |
| 10,881,863 B2 | 1/2021 | Maile et al. |

(Continued)

FOREIGN PATENT DOCUMENTS

CN 110520189 A 11/2019

OTHER PUBLICATIONS

Extended European Search Report dated Sep. 27, 2022, European Patent Application No. 22167396.5.
(Continued)

*Primary Examiner* — Nadia A Mahmood
(74) *Attorney, Agent, or Firm* — Vierra Magen Marcus LLP

(57) ABSTRACT

Certain embodiments described herein related to methods, devices, and systems that provide improved communications between first and second IMDs remotely located relative to one another and capable of communicating using both conductive communication and RF communication. Such a method can include the first IMD using conductive communication to transmit message(s) intended for the second IMD, without using RF communication, during a first period of time that a first trigger event is not detected. The method can also include the first IMD detecting the first trigger event, and in response thereto, the first IMD using RF communication to transmit message(s) intended for the second IMD during a second period of time. Thereafter, in response to first IMD detecting a second trigger event, the first IMD uses conductive communication to transmit one or more messages intended for the second IMD, without using RF communication, during a third period of time.

29 Claims, 8 Drawing Sheets

(51) Int. Cl.
*A61N 1/378* (2006.01)
*A61N 1/39* (2006.01)

(58) Field of Classification Search
USPC .......................................................... 607/32
See application file for complete search history.

(56) References Cited

U.S. PATENT DOCUMENTS

| | | | |
|---|---|---|---|
| 2007/0088405 | A1 | 4/2007 | Jacobson |
| 2007/0100396 | A1* | 5/2007 | Freeberg ............ A61N 1/37211 607/60 |
| 2012/0277818 | A1* | 11/2012 | Stancer .................. A61N 1/371 607/9 |
| 2016/0121128 | A1 | 5/2016 | Fishler et al. |
| 2016/0144190 | A1 | 5/2016 | Cao et al. |
| 2018/0168460 | A1* | 6/2018 | Morris ................. A61B 5/6882 |
| 2018/0168463 | A1 | 6/2018 | Morris et al. |
| 2018/0236249 | A1 | 8/2018 | Klimovitch et al. |
| 2020/0236620 | A1 | 7/2020 | Li et al. |
| 2020/0337563 | A1 | 10/2020 | Andersen |
| 2020/0352441 | A1 | 11/2020 | Soykan et al. |
| 2021/0093873 | A1 | 4/2021 | Chin et al. |

OTHER PUBLICATIONS

Bose, Pritam, et al., RF Channel Modeling for Implant-to-Implant Communication and Implant to Subcutaneous Implant Communication for Future Leadless Cardiac Pacemakers, IEEE Transactions on Biomedical Engineering, vol. 65, No. 12, Dec. 2018, 10 pages.
Response to Communication pursuant to Rule 69 EPC dated Sep. 27, 2022, European Patent Application No. 22167396.5.
Communication under Rule 71(3) EPC dated May 17, 2023, European Patent Application No. 22167396.5.
Office Action dated Feb. 8, 2024, Chinese Patent Application No. 202210558810.3.
English Abstract of Chinese Publication No. CN110520189 published Nov. 29, 2019.

* cited by examiner

IMPLANT TO IMPLANT COMMUNICATION FOR USE WITH IMPLANTABLE MEDICAL DEVICES

PRIORITY CLAIM

This application claims priority to U.S. Provisional Patent Application No. 63/191,854, titled IMPROVED IMPLANT TO IMPLANT COMMUNICATION FOR USE WITH IMPLANTABLE MEDICAL DEVICES, filed May 21, 2021, which is incorporated herein by references.

FIELD OF TECHNOLOGY

Embodiments described herein generally relate to methods, devices, and systems for providing and improving communication between implantable medical devices, one or more of which may be a leadless pacemaker.

BACKGROUND

Implantable medical devices (IMDs) and systems often rely on proper communication to operate correctly. For example, in a dual chamber leadless pacemaker system, implant-to-implant (i2i) communication between two or more leadless pacemakers (LPs) is critical for proper synchronization and operation of the system. The LPs can communicate with one another using conductive communication, or using i2i radio frequency (RF) communication. Conductive communication involves transmitting and receiving communication signals through patient tissue, typically using the same electrodes that are used for cardiac pacing and sensing, wherein the transmitted communication signals include pulses that can be produced using the same pulse generator that is used to produce pacing pulses. RF communication, by contrast, involves using an antenna for transmitting and receiving RF communication signals. Conductive communication, which is also known as conducted communication, or galvanic communication, is much more energy efficient than RF communication. Accordingly, the longevity of a dual chamber LP system that utilizes conducted communication for i2i communication is greater than the longevity of a dual chamber LP system that utilizes RF communication for i2i communication. However, one potential problem with relying on conducted communication for i2i communication between LPs, between an LP and another type of implantable medical device (IMD), or more generally between IMDs, is that conducted communication may be adversely affected by noise from a magnetic resonance imaging (MRI) system, or some other noise source. Accordingly, it is sometimes the case the LPs and/or other IMDs are switched into an MRI safe-mode when exposed to an MRI system, during which the LPs and/or other IMDs no longer communicate with one another. For example, a dual chamber LP system may switch from a DOO mode to a VOO mode if it is known that the LPs are about to be exposed to an MRI scan, or in response to a noise reversion trigger.

SUMMARY

Certain embodiments of the present technology are related to methods for use with a system including a first implantable medical device (IMD) and a second IMD that are remotely located relative to one another and are capable of communicating with one another using both conductive communication and radio frequency (RF) communication. Such a method can include the first IMD using conductive communication to transmit one or more messages intended for the second IMD, without using RF communication to transmit any messages intended for the second IMD, during a first period of time that a first trigger event is not detected. The method can also include the first IMD detecting the first trigger event, and in response thereto, the first IMD using RF communication to transmit one or more messages intended for the second IMD during a second period of time. The method can further include the first IMD detecting a second trigger event, and in response thereto, the first IMD using conductive communication to transmit one or more messages intended for the second IMD, without using RF communication to transmit any messages intended for the second IMD, during a third period of time.

In accordance with certain embodiments, the method includes the first IMD also using conductive communication to transmit one or more messages intended for the second IMD during the second period of time, such that during the second period of time both RF communication and conductive communication are used by the first IMD. In accordance with certain embodiments, the one or more messages intended for the second IMD, that are transmitted by the first IMD using conductive communication during the first period of time, are transmitted within a first frequency range. The one or more messages intended for the second IMD, that are transmitted by the first IMD using conductive communication during the second period of time, are also transmitted within the first frequency range. By contrast, the one or more messages intended for the second IMD, that are transmitted by the first IMD using RF communication during the second period of time, are transmitted within a second frequency range that is above the first frequency range. Beneficially, the second frequency range is above the frequencies of noise generated by an MRI system, thereby enabling the IMDs to communicate with one another using RF communication when the IMDs are subjected to noise from an MRI system.

In accordance with certain embodiments, the first trigger event comprises a magnetic resonance imaging (MRI) mode of the first IMD being activated, and the second trigger event comprises the MRI mode of the first IMD being deactivated. In certain such embodiments, the MRI mode of the first IMD is activated using a non-implanted device (e.g., an external programmer), and the MRI mode of the first IMD is deactivated using a non-implanted device that can be the same as or different than the non-implanted device that activated the MRI mode. It is also possible for the MRI mode to be deactivated in response to an MRI timeout period expiring.

In accordance with certain embodiments, the MRI mode of the first IMD is activated in response to a sensor of the first IMD detecting a magnetic field, or a surrogate thereof, that is likely generated by an MRI system. In certain such embodiments, the MRI mode of the first IMD is deactivated in response to the sensor of the first IMD no longer detecting the magnetic field, or the surrogate thereof, that is likely generated by an MRI system. It is also possible for the MRI mode to be deactivated in response to an MRI timeout period expiring.

In accordance with certain embodiments, the first trigger event comprises the first IMD determining that the second IMD did not successfully receive one or more of the messages, intended for the second IMD, that the first IMD transmitted using conductive communication. In accordance with certain such embodiments, the method further comprises the first IMD also using conductive communication to transmit one or more messages intended for the second IMD during the second period of time, as noted above. In certain such embodiments, the second trigger event comprises the first IMD determining that the second IMD successfully received at least one of the one or more messages, intended for the second IMD, that were transmitted by the first IMD using conductive communication during the second period of time. In such an embodiment, it is because that first IMD continues to transmit messages(s) using conductive communication during the second period of time that enables the first IMD to determine when the use of conductive communication is again successful, thereby enabling the first IMD to disable the less energy efficient RF communication once successful conductive communication is restored.

In accordance with certain embodiments, the first trigger event comprises a level of noise detected by the first IMD exceeding a first noise threshold, and the second trigger event comprises the level of noise detected by the first IMD being below a second noise threshold, which can be the same as or different than the first noise threshold.

In accordance with certain embodiments, the first trigger event comprises at least one of an arrhythmia being detected or arrhythmia therapy being delivered, and the second trigger event comprises at least one of the arrhythmia no longer being detected or the arrhythmia therapy being completed.

In accordance with certain embodiments, one of the first IMD and the second IMD comprises a leadless pacemaker (LP), and the other one of the first IMD and the second IMD comprises another LP, a non-vascular implantable cardioverter-defibrillator (NV-ICD), or an insertable cardiac monitor (ICM).

Certain embodiments of the present technology are directed to an IMD configured to communicate with another IMD that is remotely located relative to the IMD, wherein the IMD comprises at least two electrodes, a conductive communication transceiver, an antenna, an RF communication transceiver, and a controller. The conductive communication transceiver is coupled to the at least two electrodes and is configured to selectively transmit conductive communication messages that are intended for the other IMD, and is configured to receive conductive communication messages from the other IMD. The RF communication transceiver is coupled to the antenna and configured to selectively transmit RF communication messages that are intended for the other IMD, and configured to receive RF communication messages from the other IMD. The controller can be configured to monitor for one or more trigger events, e.g., which may include a first trigger event and a second trigger event. The controller is configured to control the conductive communication transceiver to transmit one or more conductive communication messages intended for the other IMD during a first period of time that the first trigger event is not detected. The controller is also configured to detect the first trigger event, and in response thereto, control the RF communication transceiver to transmit one or more RF communication messages intended for the other IMD during a second period of time. Additionally, the controller is configured to detect the second trigger event, and in response thereto, control the conductive communication transceiver to transmit one or more conductive communication messages intended for the other IMD during a third period of time. During the first period of time and the third period of time the RF communication transceiver is not used to transmit any RF communication messages intended for the other IMD, which has the effect of conserving power.

In accordance with certain embodiments, the conductive communication transceiver is configured to transmit and receive messages within a first frequency range, and the RF communication transceiver is configured to transmit and receive messages within a second frequency range that is above the first frequency range, as noted above.

In accordance with certain embodiments, during the first period of time the RF communication transceiver is disabled, and the conductive communication transceiver is enabled and used for both transmitting and receiving one or more messages using conductive communication.

In accordance with certain embodiments, during the second period of time both the RF communication transceiver and the conductive communication transceiver are enabled by the controller. In certain such embodiments, the controller is further configured to control the conductive communication transceiver to continue to use conductive communication to transmit one or more messages intended for the other IMD during the second period of time, such that during the second period of time both the RF communication transceiver and the conductive communication transceiver are used by the IMD to send messages to and receive messages from the other IMD.

In accordance with certain embodiments, the IMD further comprises a battery that provides power to the controller, wherein the battery also provides power to each of the conductive communication transceiver and the RF communication transceiver when they are enabled, and wherein the RF communication transceiver draws substantially no power from the battery when the RF communication transceiver is disabled.

In accordance with certain embodiments, the first trigger event comprises the controller determining that the other IMD did not successfully receive one or more of the messages, intended for the other IMD, that were transmitted by the conductive communication transceiver. In certain such embodiments, the second trigger event comprises the controller determining that the other IMD successfully received at least one of one or more messages, intended for the other IMD, that were transmitted by the conductive communication transceiver during the second period of time.

In accordance with certain embodiments, the first trigger event comprises an MRI mode of the IMD being activated, and the second trigger event comprises the MRI mode of the IMD being deactivated. In certain such embodiments, the MRI mode of the IMD can be selectively activated and deactivated by a non-implanted device (e.g., an external programmer).

In accordance with certain embodiments, the first trigger event comprises at least one of an arrhythmia being detected or arrhythmia therapy being delivered by the IMD or the other IMD, and the second trigger event comprises at least one of the arrhythmia no longer being detected or the arrhythmia therapy being completed.

In accordance with certain embodiments, the IMD further comprises a sensor configured to detect a magnetic field, or a surrogate thereof, that is likely generated by an MRI system. For example, the IMD can include a magnetic field sensor, such as a Hall effect sensor, a giant magnetoresistance (GMR) sensor, or a reed switch. Alternatively, or additionally, the IMD can include an accelerometer type sensor that can detect a surrogate of the magnetic field that is likely generated by an MRI system. In certain such embodiments, the controller is configured to activate the MRI mode in response to the sensor detecting the magnetic field, or the surrogate thereof, that is likely generated by an MRI system. Additionally, the controller is configured to deactivate the MRI mode in response to the sensor no longer detecting the magnetic field, or the surrogate thereof, that is likely generated by an MRI system. The controller can alternatively, or additionally, be configured to deactivate the MRI mode in response to an MRI timeout period expiring.

In accordance with certain embodiments, the first trigger event comprises a level of noise detected by the IMD exceeding a first noise threshold, and the second trigger event comprises the level of noise detected by the IMD being below a second noise threshold, which can be the same as or different than the first noise threshold.

In accordance with certain embodiments, the IMD comprises one of an LP, a non-vascular ICD, or an ICM. Other variations are also possible and within the scope of the embodiments described herein.

Certain embodiments of the present technology are directed to a system comprising a first IMD and a second IMD that are configured to be implanted at different locations within a patient, such as in or on different cardiac chambers of the heart. Each IMD, of the first and the second IMDs, includes a conductive communication transceiver and an RF communication transceiver. The conductive communication transceiver of each IMD is configured to transmit and receive i2i messages using conductive communication. The RF communication transceiver of each IMD is configured to transmit and receive i2i messages using RF communication while the RF communication transceiver is enabled. In certain such embodiments, each IMD, of the first and second IMDs, is configured to use the conductive communication transceiver of the IMD without using the RF communication transceiver of the IMD to send and receive i2i messages during a period of time that a first trigger event is not detected. Additionally, each IMD, of the first and the second IMDs, is configured to use both the conductive communication transceiver and the RF communication transceiver of the IMD to send and receive i2i messages during a further period of time, in response to the first trigger event being detected.

This summary is not intended to be a complete description of the embodiments of the present technology. Other features and advantages of the embodiments of the present technology will appear from the following description in which the preferred embodiments have been set forth in detail, in conjunction with the accompanying drawings and claims.

BRIEF DESCRIPTION OF THE DRAWINGS

Embodiments of the present technology relating to both structure and method of operation may best be understood by referring to the following description and accompanying drawings, in which similar reference characters denote similar elements throughout the several views.

DETAILED DESCRIPTION

Certain embodiments of the present technology related to implantable medical devices (IMDs), and methods for use therewith, that improve implant-to-implant (i2i) communication between the IMDs, one or more of which may be a leadless pacemaker (LP). Before providing additional details of the specific embodiments of the present technology mentioned above, an example system in which embodiments of the present technology can be used will first be described with reference to FIGS. 1-5. More specifically, FIGS. 1-5 will be used to describe an example cardiac pacing system, wherein pacing and sensing operations can be performed by multiple medical devices, which may include one or more leadless cardiac pacemakers, a non-vascular ICD, such as a subcutaneous-ICD (S-ICD), and/or a programmer to reliably and safely coordinate pacing and/or sensing operations. A leadless cardiac pacemaker can also be referred to more succinctly herein as a leadless pacemaker (LP). Where a cardiac pacing system includes a non-vascular ICD (e.g., an S-ICD), the non-vascular ICD may perform certain sensing operations and may communicate with one or more LPs by sending and/or receiving messages to and/or from one or more LPs, as can be appreciated from the below discussion. Where a cardiac pacing system includes a programmer, the programmer may be used to program one or more IMDs, download information to one or more IMDs, and/or upload information from one or more IMDs, as can be appreciated from the below description.

Figure 1:
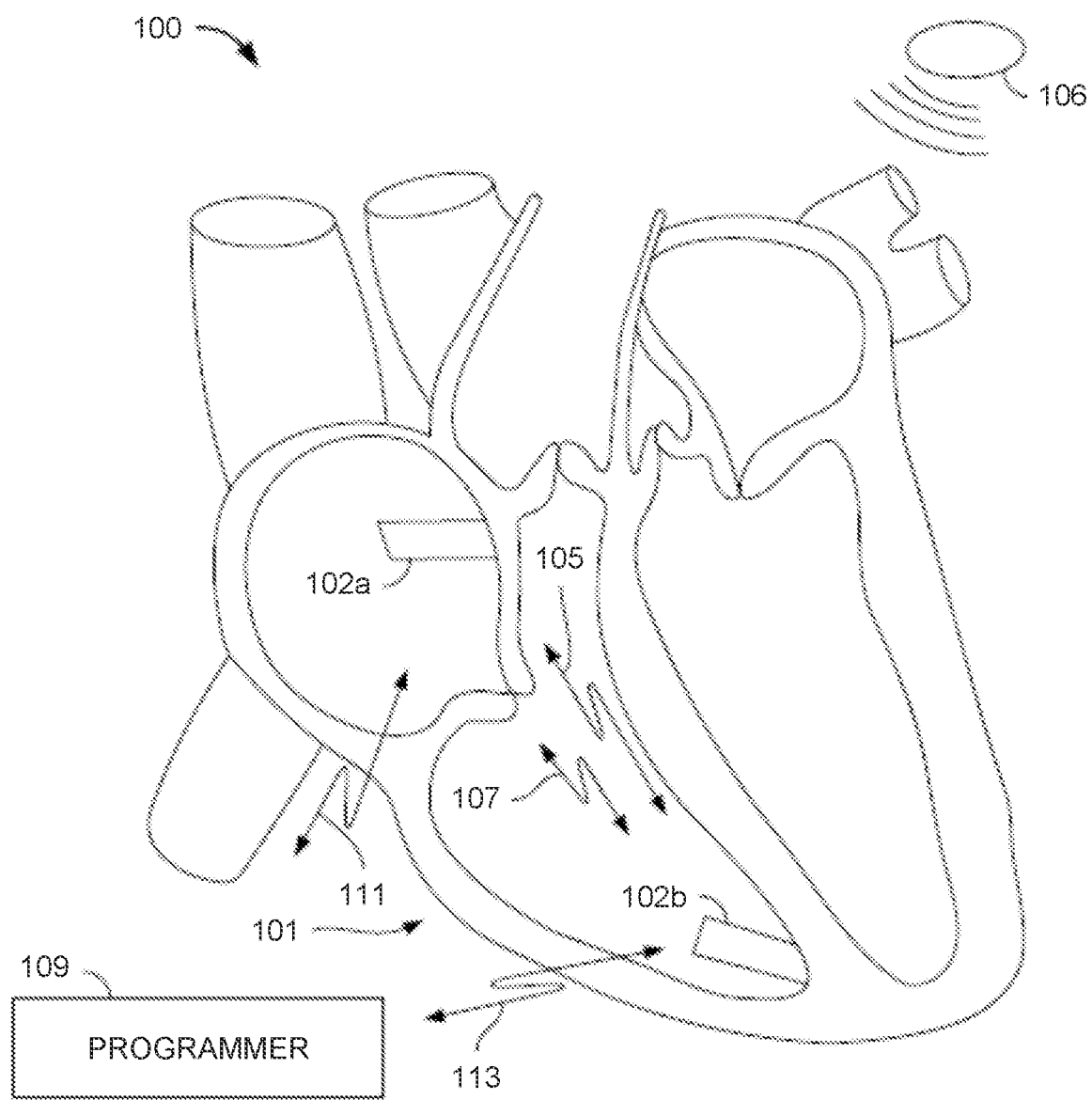
FIG. 1 illustrates a system formed in accordance with certain embodiments herein as implanted in a heart.

FIG. 1 illustrates a system 100 that is configured to be implanted in a heart 101. The system 100 includes two or more leadless pacemakers (LPs) 102a and 102b located in different chambers of the heart. LP 102a is located in a right atrium, while LP 102b is located in a right ventricle. LPs 102a and 102b communicate with one another to inform one another of various local physiologic activities, such as local intrinsic events, local paced events and the like. LPs 102a and 102b may be constructed in a similar manner, but operate differently based upon which chamber the LP 102a or 102b is located. The LPs 102a and 102b may sometimes be referred to collectively herein as the LPs 102, or individually as an LP 102.

In certain embodiments, LPs 102a and 102b communicate with one another, and/or with an ICD 106, by conductive communication through the same electrodes that are used for sensing and/or delivery of pacing therapy. The LPs 102a and 102b may also be able to use conductive communication to communicate with an external device, e.g., a programmer 109, having electrodes placed on the skin of a patient within with the LPs 102a and 102b are implanted. The LPs 102a and 102b can each also include an antenna that would enable them to communicate with one another, the ICD 106 and/or an external device using RF communication. While only two LPs are shown in FIG. 1, it is possible that more than two LPs can be implanted in a patient. For example, to provide for bi-ventricular pacing and/or cardiac resynchronization therapy (CRT), in addition to having LPs implanted in the right atrial (RA) chamber and the right ventricular (RV) chamber, a further LP can be implanted in the left ventricular (LV) chamber.

In some embodiments, one or more LP 102 can be co-implanted with the ICD 106. Each LP 102 uses two or more electrodes located within, on, or within a few centimeters of the housing of the pacemaker, for pacing and sensing at the cardiac chamber, for bidirectional conductive communication with one another, with the programmer 109, and the ICD 106.

While the methods, devices and systems described herein include examples primarily in the context of LPs, it is understood that the methods, devices and systems described herein may be utilized with various other types of IMDs. In other words, the methods, devices and systems may be used to improve communication between various IMDs implanted in a human, not just LPs. For examples, such embodiments can be used to improve communications between at least two LPs, between an LP and an NV-ICD, between an LP and an ICM, between an ICM and an S-ICD, but are not limited thereto. It should also be understood that the embodiments described herein can be used to improve communication between more than two IMDs, and are not limited to communication between just first and second IMDs. The methods, devices and systems may also be used to improve communication between two or more IMDs implanted within the same cardiac chamber that may be the same type of IMD or may be different types of IMDs. The methods, devices and systems may also be used to improve communication between two or more IMDs in a system including at least one IMD that is not implanted within a cardiac chamber, but rather, is implanted epicardially, transmurally, intravascularly (e.g., coronary sinus), or subcutaneously (e.g., S-ICD), etc.

Figure 2:
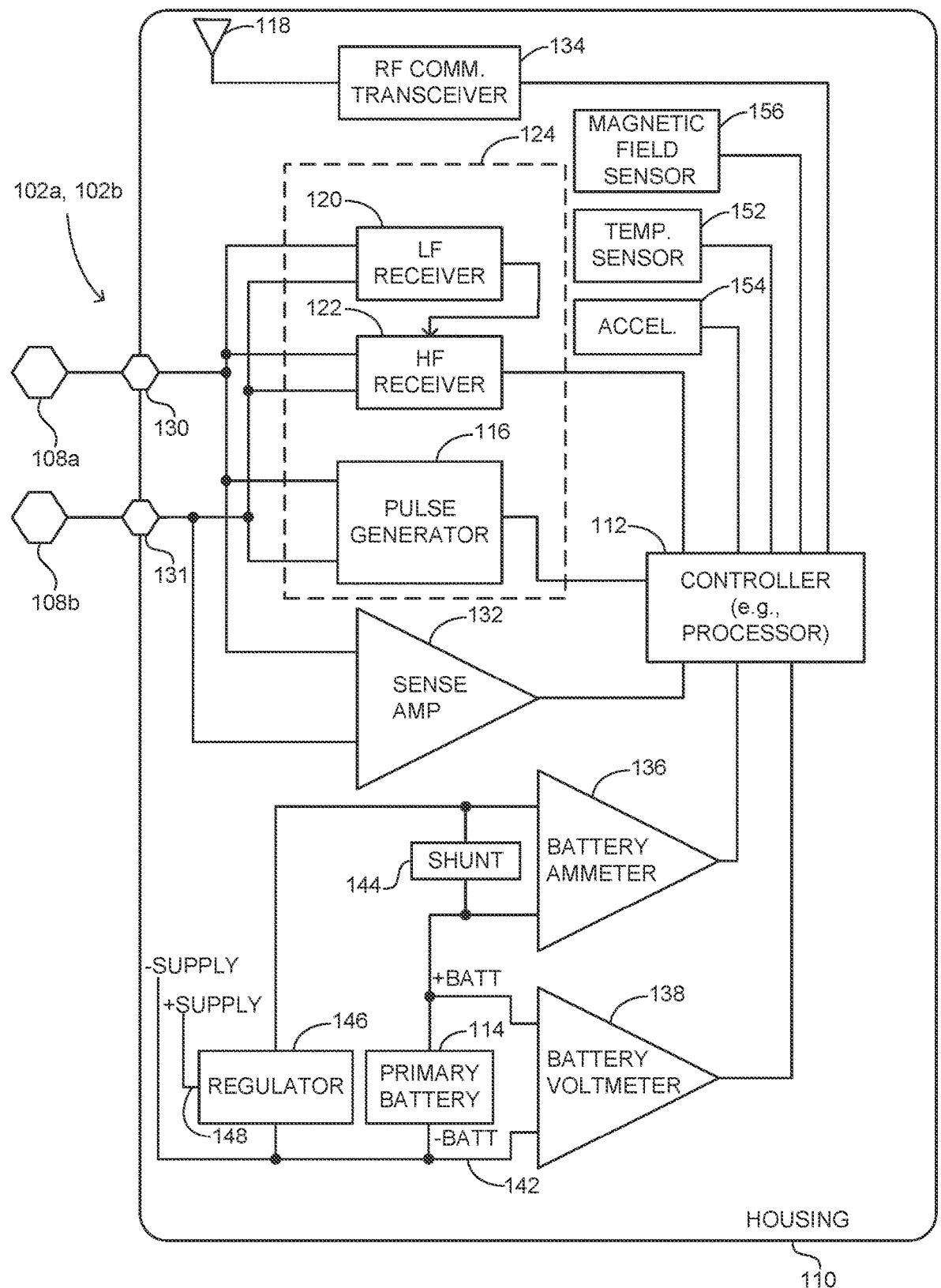
FIG. 2 is a block diagram of a single LP in accordance with certain embodiments herein.

Referring to FIG. 2, a block diagram shows an embodiment for portions of the electronics within LPs 102a, 102b configured to provide conductive communication through the sensing/pacing electrode. One or more of LPs 102a and 102b include at least two leadless electrodes configured for delivering cardiac pacing pulses, sensing evoked and/or natural cardiac electrical signals, and uni-directional or bi-directional conductive communication. In FIG. 2 (and FIG. 3) the two electrodes shown therein are labeled 108a and 108b. Such electrodes can be referred to collectively as the electrodes 108, or individually as an electrode 108. An LP 102, or other type of IMD, can include more than two electrodes 108, depending upon implementation.

In FIG. 2, each of the LPs 102a, 102b is shown as including first and second receivers 120 and 122 that collectively define separate first and second conductive communication channels 105 and 107 (FIG. 1), (among other things) between LPs 102a and 102b. Although first and second receivers 120 and 122 are depicted, in other embodiments, each LP 102a, 102b may only include the first receiver 120, or more generally may include only a single receiver that is configured to receive conductive communication signals. It is also possible that an LP 102 may include additional receivers other than first and second receivers 120 and 122. As will be described in additional detail below, the pulse generator 116 can function as a transmitter that transmits i2i communication signals using the electrodes 108. In certain embodiments, LPs 102a and 102b may communicate over more than just first and second conductive communication channels 105 and 107. In certain embodiments, LPs 102a and 102b may communicate over one common communication channel 105. More specifically, LPs 102a and 102b can communicate conductively over a common physical channel via the same electrodes 108 that are also used to deliver pacing pulses.

The receivers 120 and 122 can also be referred to, respectively, as a low frequency (LF) receiver 120 and a high frequency (HF) receiver 122, because the receiver 120 is configured to monitor for one or more signals within a relatively low frequency range (e.g., below 100 KHz) and the receiver 122 is configured to monitor for one or more signals within a relatively high frequency range (e.g., above 100 KHz). In certain embodiments, the receiver 120 (and more specifically, at least a portion thereof) is always enabled and monitoring for a wakeup notice, which can simply be a wakeup pulse, within a specific low frequency range (e.g., between 1 KHz and 100 KHz); and the receiver 122 is selectively enabled by the receiver 120. The receiver 120 is configured to consume less power than the receiver 122 when both the first and second receivers are enabled. Accordingly, the receiver 120 can also be referred to as a low power receiver 120, and the receiver 122 can also be referred to as a high power receiver 122. The low power receiver 120 is incapable of receiving signals within the relatively high frequency range (e.g., above 100 KHz), but consumes significantly less power than the high power receiver 122. This way the low power receiver 120 is capable of always monitoring for a wakeup notice without significantly depleting the battery (e.g., 114) of the LP. In accordance with certain embodiments, the high power receiver 122 is selectively enabled by the low power receiver 120, in response to the low power receiver 120 receiving a wakeup notice, so that the high power receiver 122 can receive the higher frequency signals, and thereby handle higher data throughput needed for effective i2i communication without unnecessarily and rapidly depleting the battery of the LP (which the high power receiver 122 may do if it were always enabled).

Since the receivers 120, 122 are used to receive conductive communication messages, the receivers 120, 122 can also be referred to as conductive communication receivers. In certain embodiments, each of the LPs 102 includes only a single conductive communication receiver.

In accordance with certain embodiments, when one of the LPs 102a and 102b senses an intrinsic event or delivers a paced event, the corresponding LP 102a, 102b transmits an implant event message to the other LP 102a, 102b. For example, when an atrial LP 102a senses/paces an atrial event, the atrial LP 102a transmits an implant event message including an event marker indicative of a nature of the event (e.g., intrinsic/sensed atrial event, paced atrial event). When a ventricular LP 102b senses/paces a ventricular event, the ventricular LP 102b transmits an implant event message including an event marker indicative of a nature of the event (e.g., intrinsic/sensed ventricular event, paced ventricular event). In certain embodiments, each LP 102a, 102b transmits an implant event message to the other LP 102a, 102b preceding the actual pace pulse so that the remote LP can blank its sense inputs in anticipation of that remote pace pulse (to prevent inappropriate crosstalk sensing). The above describe implant event messages are examples of i2i messages.

The implant event messages may be formatted in various manners. As one example, each event message may include a leading trigger pulse (also referred to as an LP wakeup notice, wakeup pulse or wakeup signal) followed by an event marker. The notice trigger pulse (also referred to as the wakeup notice, wakeup pulse or wakeup signal) is transmitted over a first channel (e.g., with a pulse duration of approximately 10 µs to approximately 1 ms and/or within a fundamental frequency range of approximately 1 KHz to approximately 100 KHz). The notice trigger pulse indicates that an event marker is about to be transmitted over a second channel (e.g., within a higher frequency range). The event marker can then be transmitted over the second channel.

The event markers may include data indicative of one or more events (e.g., a sensed intrinsic atrial activation for an atrial located LP, a sensed intrinsic ventricular activation for a ventricular located LP). The event markers may include different markers for intrinsic and paced events. The event markers may also indicate start or end times for timers (e.g., an AV interval, a blanking interval, etc.). Optionally, the implant event message may include a message segment that includes additional/secondary information.

Optionally, the LP (or other IMD) that receives any i2i communication message from another LP (or other IMD) or from an external device may transmit a receive acknowledgement indicating that the receiving LP (or other IMD) received the i2i communication message. In certain embodiments, where an IMD expects to receive an i2i communication message within a window, and fails to receive the i2i communication message within the window, the IMD may transmit a failure-to-receive acknowledgement indicating that the receiving IMD failed to receive the i2i communication message. In other words, an LP can receive a message from another LP that includes an indicator (e.g., an error code) in its payload, or header, that indicates to the LP that the other LP failed to receive an expected message from the LP. Other variations are also possible and within the scope of the embodiments described herein.

The event messages enable the LPs 102a, 102b to deliver synchronized therapy and additional supportive features (e.g., measurements, etc.). To maintain synchronous therapy, each of the LPs 102a and 102b is made aware (through the event messages) when an event occurs in the chamber containing the other LP 102a, 102b. Some embodiments described herein provide efficient and reliable processes to maintain synchronization between LPs 102a and 102b without maintaining continuous communication between LPs 102a and 102b. In accordance with certain embodiments herein, low power event messages/signaling may be maintained between LPs 102a and 102b synchronously or asynchronously.

For synchronous event signaling, LPs 102a and 102b may maintain synchronization and regularly communicate at a specific interval. Synchronous event signaling allows the transmitter and receivers in each LP 102a,102b to use limited (or minimal) power as each LP 102a, 102b is only powered for a small fraction of the time in connection with transmission and reception. For example, LP 102a, 102b may transmit/receive (Tx/Rx) communication messages in time slots having duration of 10-20 µs, where the Tx/Rx time slots occur periodically (e.g., every 10-20 ms).

LPs 102a and 102b may lose synchronization, even in a synchronous event signaling scheme. As explained herein, features may be included in LPs 102a and 102b to maintain device synchronization, and when synchronization is lost, LPs 102a and 102b undergo operations to recover synchronization. Also, synchronous event messages/signaling may introduce a delay between transmissions which causes a reaction lag at the receiving LP 102a, 102b. Accordingly, features may be implemented to account for the reaction lag.

During asynchronous event signaling, LPs 102a and 102b do not maintain communication synchronization. During asynchronous event signaling, one or more of receivers 120 and 122 of LPs 102a and 102b may be "always on" (always awake) to search for incoming transmissions. However, maintaining LP receivers 120, 122 in an "always on" (always awake) state presents challenges as the received signal level often is low due to high channel attenuation caused by the patient's anatomy. Further, maintaining the receivers awake will deplete the battery 114 more quickly than may be desirable.

The asynchronous event signaling methods avoid risks associated with losing synchronization between devices. However, the asynchronous event signaling methods utilize additional receiver current between transmissions. For purposes of illustration only, a non-limiting example is described hereafter. For example, the channel attenuation may be estimated to have a gain of $\frac{1}{500}$ to $\frac{1}{10000}$. A gain factor may be $\frac{1}{1000}$th. Transmit current is a design factor in addition to receiver current. As an example, the system may allocate one-half of the implant communication current budget to the transmitter (e.g., 0.5 µA for each transmitter). When LP 102a, 102b maintains a transmitter in a continuous on-state and the electrode load is 500 ohms, a transmitted voltage may be 2.5V. When an event signal is transmitted at 2.5V, the event signal is attenuated as it propagates and would appear at LP 102a, 102b receiver as an amplitude of approximately 0.25 mV.

To overcome the foregoing receive power limit, a pulsed transmission scheme may be utilized in which communication transmissions occur correlated with an event. By way of example, the pulsed transmission scheme may be simplified such that each transmission constitutes a single pulse of a select amplitude and width.

In accordance with certain embodiments herein, LPs 102a and 102b may utilize multi-stage receivers that implement a staged receiver wakeup scheme in order to improve reliability yet remain power efficient. Each of LPs 102a and 102b may include first and second receivers 120 and 122 that operate with different first and second activation protocols and different first and second receive channels. For example, first receiver 120 may be assigned a first activation protocol that is "always on" (also referred to as always awake) and that listens over a first receive channel that has a lower fundamental frequency range/pulse duration (e.g., 1 KHz to 100 KHz/10 µs to approximately 1 ms) as compared to the fundamental frequency range (e.g., greater than 100 KHz/less than 10 µs per pulse) assigned to the second receive channel.

In accordance with certain embodiments, the first receiver 120 may maintain the first channel active (awake) at all times (including when the second channel is inactive (asleep)) in order to listen for messages from a remote LP. The second receiver 122 may be assigned a second activation protocol that is a triggered protocol, in which the second receiver 122 becomes active (awake) in response to detection of trigger events over the first receive channel (e.g., when the incoming signal corresponds to the LP wakeup notice, activating the second channel at the local LP). The terms active, turned on, awake and enabled are used interchangeably herein.

Still referring to FIG. 2, each LP 102a, 102b is shown as including a controller 112 and a pulse generator 116. The controller 112 can include, e.g., a microprocessor (or equivalent control circuitry), RAM and/or ROM memory, logic and timing circuitry, state machine circuitry, and I/O circuitry, but is not limited thereto. The controller 112 can further include, e.g., timing control circuitry to control the timing of the stimulation pulses (e.g., pacing rate, atrio-ventricular (AV) delay, atrial interconduction (A-A) delay, or ventricular interconduction (V-V) delay, etc.). Such timing control circuitry may also be used for the timing of refractory periods, blanking intervals, noise detection windows, evoked response windows, alert intervals, marker channel timing, and so on. The controller 112 can further include other dedicated circuitry and/or firmware/software components that assist in monitoring various conditions of the patient's heart and managing pacing therapies. For example, the controller 112 can include an arrhythmia detector, which can be similar to the arrhythmia detector 834 discussed below with reference to FIG. 8.

The controller 112 and the pulse generator 116 may be configured to transmit event messages, via the electrodes 108, in a manner that does not inadvertently capture the heart in the chamber where LP 102*a*, 102*b* is located, such as when the associated chamber is not in a refractory state. In addition, an LP 102*a*, 102*b* that receives an event message may enter an "event refractory" state (or event blanking state) following receipt of the event message. The event refractory/blanking state may be set to extend for a determined period of time after receipt of an event message in order to avoid the receiving LP 102*a*, 102*b* from inadvertently sensing another signal as an event message that might otherwise cause retriggering. For example, the receiving LP 102*a*, 102*b* may detect a measurement pulse from another LP 102*a*, 102*b* or the programmer 109.

Since the conductive communication receivers 120, 122 (or alternatively, just a single conductive communication receiver) and the pulse generator 116 are used to perform conductive communication, these components can be considered parts of a conductive communication transceiver 124. The conductive communication transceiver 124 can alternatively include alternative and/or additional components that enable an LP, or other type of IMD, to transmit and receive conductive communication messages with another IMD and/or with an external device, such as the programmer 109. For an example, while the same pulse generator 116 can be used to produce pacing pulses (for use in pacing a patient's heart) and conductive communication pulses (for use in communicating with another IMD or an external device), it would also be possible that the conductive communication transceiver 124 can include its own dedicated pulse generator. For another example, as noted above, it would also be possible for the conductive communication transceiver 124 to include only a single receiver, rather than both receivers 120, 122. Other variations are also possible and within the scope of the embodiments described herein.

Still referring to FIG. 2, the LP 102 is also shown as including an antenna 118 that is coupled to a radio frequency (RF) communication transceiver 134, which is configured to transmit and receive RF communication messages using an RF communication protocol, such as a Bluetooth protocol, WiFi protocol, Bluetooth low energy (BLE) protocol, Medical Device Radiocommunications Service (MedRadio) protocol, and/or the like. In certain embodiments, the antenna 118 can be integrated into a fixation mechanism (e.g., 205) of the LP, in which case the antenna can be referred to as a fixation antenna. An example implementation of a fixation antenna is disclosed in U.S. Pat. No. 10,583,300, titled "Leadless implantable medical device with fixation antenna member," which is incorporated herein by reference. In other embodiments, the antenna 118 is separate and distinct from the fixation mechanism of the LP 102. The specific type, location and formfactor of the antenna may depend on the specific type and formfactor of the IMD.

The RF communication transceiver 134 consumes more battery power than the conductive communication transceiver 124. More generally, it is more power efficient from an LP 102 (or other type of IMD) to use conductive communication than to use RF communication to communicate with another LP 102 (or other type of IMD). Accordingly, in accordance with certain embodiments of the present technology, the LP 102 (or other type of IMD) is configured to primarily transmit and receive messages using conductive communication, and RF communication is used as a backup or auxiliary type of communication that can be used when conductive communication is deactivated (aka turned off) or is unsuccessful or otherwise deficient, as will be described in additional detail below.

In accordance with certain embodiments herein, the programmer 109 may communicate over a programmer-to-LP channel, with LP 102*a*, 102*b* utilizing the same communication scheme. The external programmer 109 may listen to the event message transmitted between LP 102*a*, 102*b* and synchronize programmer to implant communication such that programmer 109 does not transmit communication messages 113 until after an i2i messaging sequence is completed.

In accordance with certain embodiments, LP 102*a*, 102*b* may combine transmit operations with therapy. The transmit event marker may be configured to have similar characteristics in amplitude and pulse-width to a pacing pulse and LP 102*a*, 102*b* may use the energy in the event messages to help capture the heart. For example, a pacing pulse may normally be delivered with pacing parameters of 2.5V amplitude, 500 ohm impedance, 60 bpm pacing rate, 0.4 ms pulse-width. The foregoing pacing parameters correspond to a current draw of about 1.9 µA. The same LP 102*a*, 102*b* may implement an event message utilizing event signaling parameters for amplitude, pulse-width, pulse rate, etc. that correspond to a current draw of approximately 0.5 µA for transmit.

LP 102*a*, 102*b* may combine the event message transmissions with pacing pulses. For example, LP 102*a*, 102*b* may use a 50 µs wakeup transmit pulse having an amplitude of 2.5V which would draw 250 nC (nano Coulombs) for an electrode load of 500 ohm. The pulses of the transmit event message may be followed by an event message encoded with a sequence of short duration pulses (for example 16, 2 µs on/off bits) which would draw an additional 80 nC. The event message pulse would then be followed by the remaining pulse-width needed to reach an equivalent charge of a nominal 0.4 ms pace pulse. In this case, the current necessary to transmit the marker is essentially free as it was used to achieve the necessary pace capture anyhow. With this method, the savings in transmit current could be budgeted for the receiver or would allow for additional longevity.

When LP 102*a* or 102*b* senses an intrinsic event, it can send a qualitatively similar event pulse sequence (but indicative of a sensed event) without adding the pace pulse remainder. As LP 102*a*, 102*b* longevity calculations are designed based on the assumption that LP 102*a*, 102*b* will deliver pacing therapy 100% of the time, transmitting an intrinsic event marker to another LP 102*a*, 102*b* will not impact the nominal calculated LP longevity.

In some embodiments, LP 102*a*, 102*b* may deliver pacing pulses at relatively low amplitude. When low amplitude pacing pulses are used, the power budget for event messages may be modified to be a larger portion of the overall device energy budget. As the pacing pulse amplitude is lowered closer to amplitude of event messages, LP 102*a*, 102*b* increases an extent to which LP 102*a*, 102*b* uses the event messages as part of the pacing therapy (also referred to as sharing "capture charge" and "transmit charge"). As an example, if the nominal pacing voltage can be lowered to <1.25 V, then a "supply halving" pacing charge circuit could reduce the battery current draw by approximately 50%. A 1.25V pace pulse would save 1.5 µA of pacing current budget. With lower pulse amplitudes, LP 102a, 102b may use larger pulse-widths.

By combining event messages and low power pacing, LP 102a, 102b may realize additional longevity. Today longevity standards provide that the longevity to be specified based on a therapy that utilizes 2.5V amplitude, 0.4 ms pulses at 100% pacing. Optionally, a new standard may be established based on pacing pulses that deliver lower amplitude and/or shorter pacing pulses.

While not shown, a communication capacitor can be provided in LP 102a, 102b. The communication capacitor may be used to transmit event signals having higher voltage for the event message pulses to improve communication, such as when the LPs 102a and 102b experience difficulty sensing event messages. The high voltage event signaling may be used for implants with high signal attenuation or in the case of a retry for an ARQ (automatic repeat request) handshaking scheme.

In some embodiments, each individual LP 102 can comprise a hermetic housing 110 configured for placement on or attachment to the inside or outside of a cardiac chamber and at least two leadless electrodes 108 proximal to the housing 110 and configured for bidirectional communication with at least one other device (e.g., an NV-ICD 106) within or outside the body.

FIG. 2 depicts a single LP 102 (e.g., the LP 102a or 102b) and shows the LP's functional elements substantially enclosed in a hermetic housing 110. The LP 102 has at least two electrodes 108 located within, on, or near the housing 110, for delivering pacing pulses to and sensing electrical activity from the muscle of the cardiac chamber, and for bidirectional communication with at least one other device within or outside the body. Hermetic feedthroughs 130, 131 conduct electrode signals through the housing 110. The housing 110 contains a primary battery 114 to supply power for pacing, sensing, and communication. The housing 110 also contains circuits 132 for sensing cardiac activity from the electrodes 108, receivers 120, 122 for receiving information from at least one other device via the electrodes 108, and the pulse generator 116 for generating pacing pulses for delivery via the electrodes 108 and also for transmitting information to at least one other device via the electrodes 108. The housing 110 can further contain circuits for monitoring device health, for example a battery current monitor 136 and a battery voltage monitor 138, and can contain circuits for controlling operations in a predetermined manner.

The electrodes 108 can be configured to communicate bidirectionally among the multiple leadless cardiac pacemakers and/or the implanted ICD 106 to coordinate pacing pulse delivery and optionally other therapeutic or diagnostic features using messages that identify an event at an individual pacemaker originating the message and a pacemaker receiving the message react as directed by the message depending on the origin of the message. An LP 102a, 102b that receives the event message reacts as directed by the event message depending on the message origin or location. In some embodiments or conditions, the two or more leadless electrodes 108 can be configured to communicate bidirectionally among the one or more leadless cardiac pacemakers 102 and/or the ICD 106 and transmit data including designated codes for events detected or created by an individual pacemaker. Individual pacemakers can be configured to issue a unique code corresponding to an event type and a location of the sending pacemaker.

In some embodiments, an individual LP 102a, 102b can be configured to deliver a pacing pulse with an event message encoded therein, with a code assigned according to pacemaker location and configured to transmit a message to one or more other leadless cardiac pacemakers via the event message coded pacing pulse. The pacemaker or pacemakers receiving the message are adapted to respond to the message in a predetermined manner depending on type and location of the event.

Moreover, information communicated on the incoming channel can also include an event message from another leadless cardiac pacemaker signifying that the other leadless cardiac pacemaker has sensed a heartbeat or has delivered a pacing pulse, and identifies the location of the other pacemaker. For example, LP 102b may receive and relay an event message from LP 102a to the programmer. Similarly, information communicated on the outgoing channel can also include a message to another leadless cardiac pacemaker or pacemakers, or to the ICD, that the sending leadless cardiac pacemaker has sensed a heartbeat or has delivered a pacing pulse at the location of the sending pacemaker.

Referring again to FIGS. 1 and 2, the cardiac pacing system 100 may comprise an ICD 106 in addition to one or more LPs 102a, 102b configured for implantation in electrical contact with a cardiac chamber and for performing cardiac rhythm management functions in combination with the implantable ICD 106. The implantable ICD 106 and the one or more LPs 102a, 102b configured for leadless intercommunication by information conduction through body tissue and/or wireless transmission between transmitters and receivers in accordance with the embodiments discussed herein.

In a further embodiment, a cardiac pacing system 100 comprises at least one LP 102a, 102b configured for implantation in electrical contact with a cardiac chamber and configured to perform cardiac pacing functions in combination with the co-implanted ICD 106. Each LP 102 comprise at least two leadless electrodes 108 configured for delivering cardiac pacing pulses, sensing evoked and/or natural cardiac electrical signals, and transmitting information to the co-implanted ICD 106.

As shown in the illustrative embodiments, an LP 102a, 102b can comprise two or more leadless electrodes 108 configured for delivering cardiac pacing pulses, sensing evoked and/or natural cardiac electrical signals, and bidirectionally communicating with the co-implanted ICD 106.

Each LP 102a, 102b can be configured for operation in a respective particular location and to have a respective particular functionality at manufacture and/or by programming by an external programmer. Bidirectional communication among the multiple leadless cardiac pacemakers can be arranged to communicate notification of a sensed heartbeat or delivered pacing pulse event and encoding type and location of the event to another implanted pacemaker or pacemakers. The LP 102a, 102b receiving the communication decode the information and respond depending on location of the receiving pacemaker and predetermined system functionality.

In some embodiments, the LPs 102a and 102b are configured to be implantable in any chamber of the heart, namely either atrium (RA, LA) or either ventricle (RV, LV). Furthermore, for dual-chamber configurations, multiple LPs may be co-implanted (e.g., one in the RA and one in the RV, one in the RV and one in the coronary sinus proximate the LV). Certain pacemaker parameters and functions depend on (or assume) knowledge of the chamber in which the pacemaker is implanted (and thus with which the LP is interacting; e.g., pacing and/or sensing). Some non-limiting examples include sensing sensitivity, an evoked response algorithm, use of AF suppression in a local chamber, blanking & refractory periods, etc. Accordingly, each LP needs to know an identity of the chamber in (or on) which the LP is implanted, and processes may be implemented to automatically identify a local chamber associated with each LP.

Processes for chamber identification may also be applied to subcutaneous pacemakers, ICDs, with leads and the like. A device with one or more implanted leads, identification and/or confirmation of the chamber into which the lead was implanted could be useful in several pertinent scenarios. For example, for a DR or CRT device, automatic identification and confirmation could mitigate against the possibility of the clinician inadvertently placing the V lead into the A port of the implantable medical device, and vice-versa. As another example, for an SR device, automatic identification of implanted chamber could enable the device and/or programmer to select and present the proper subset of pacing modes (e.g., AAI or VVI), and for the IPG to utilize the proper set of settings and algorithms (e.g., V-AutoCapture vs ACap-Confirm, sensing sensitivities, etc.).

Also shown in FIG. 2, the primary battery 114 has positive terminal 140 and negative terminal 142. Current from the positive terminal 140 of primary battery 114 flows through a shunt 144 to a regulator circuit 146 to create a positive voltage supply 148 suitable for powering the remaining circuitry of the pacemaker 102. The shunt 144 enables the battery current monitor 136 to provide the controller 112 with an indication of battery current drain and indirectly of device health. The illustrative power supply can be a primary battery 114.

Still referring to FIG. 2, the LP is shown as including a temperature sensor 152. The temperature sensor can be any one of various different types of well-known temperature sensors, or can be a future developed temperature sensor. For one example, the temperature sensor 152 can be a thermistor, a thermocouple, a resistance thermometer, or a silicon bandgap temperature sensor, but is not limited thereto. Regardless of how the temperature sensor 152 is implemented, it is preferably that the temperature sensed by the sensor is provided to the controller 112 as a digital signal indicative of the blood temperature of the patient within which the LP is implanted. The temperature sensor 152 can be hermetically sealed within the housing 110, but that need not be the case. The temperature sensor 152 can be used in various manners. For example, the temperature sensor 152 can be used to detect an activity level of the patient to adjust a pacing rate, i.e., for use in rate responsive pacing. When a person starts to exercise their core body temperature initially dips, and then after exercising for a prolonged period of time the person's core body temperature will eventually rise. Thereafter, when the person stops exercising their core body temperature will return to its baseline. Accordingly, the controller 112 can be configured to detect an activity level of a patient based on core blood temperature measurements obtained using the temperature sensor 152.

Referring to FIG. 2, the LP is also shown as including an accelerometer 154 which can be hermetically contained within the housing 110. The accelerometer 154 can be any one of various different types of well-known accelerometers, or can be a future developed accelerometer. For one example, the accelerometer 154 can be or include, e.g., a MEMS (micro-electromechanical system) multi-axis accelerometer of the type exploiting capacitive or optical cantilever beam techniques, or a piezoelectric accelerometer that employs the piezoelectric effect of certain materials to measure dynamic changes in mechanical variables. For example, the accelerometer 154 can be used to detect an activity level of the patient to adjust a pacing rate, i.e., for use in rate responsive pacing. It would also be possible to use outputs of both the accelerometer 154 and the temperature sensor 152 to monitor the activity level of a patient. Alternatively, or additionally, a patient's activity level can be monitored based on their heart rate, as detected from an IEGM sensed using the electrodes 108, and/or sensed using a plethysmography signal obtained using a plethysmography sensor (not shown) or a heart sound sensor (not shown), but not limited thereto. One or more signals produced and output by the accelerometer 154 may be analyzed with respect to frequency content, energy, duration, amplitude and/or other characteristics. Such signals may or may not be amplified and/or filtered prior to being analyzed. For example, filtering may be performed using lowpass, highpass and/or bandpass filters. The signals output by the accelerometer 154 can be analog signals, which can be analyzed in the analog domain, or can be converted to digital signals (by an analog-to-digital converter) and analyzed in the digital domain. Alternatively, the signals output by the accelerometer 154 can already be in the digital domain. The one or more signals output by the accelerometer 154 can be analyzed by the controller 112 and/or other circuitry. In certain embodiments, the accelerometer 154 is packaged along with an integrated circuit (IC) that is designed to analyze the signal(s) it generates. In such embodiments, one or more outputs of the packaged sensor/IC can be an indication of acceleration along one or more axes. In other embodiments, the accelerometer 154 can be packaged along with an IC that performs signal conditioning (e.g., amplification and/or filtering), performs analog-to-digital conversions, and stores digital data (indicative of the sensor output) in memory (e.g., RAM, which may or may not be within the same package). In such embodiments, the controller 112 or other circuitry can read the digital data from the memory and analyze the digital data. Other variations are also possible, and within the scope of embodiments of the present technology. In accordance with certain embodiments of the present technology, described in additional detail below, a sensor signal produced by the accelerometer 154 of an LP implanted in or on a cardiac chamber can be used to detect mechanical cardiac activity associated with another cardiac chamber.

Still referring to FIG. 2, the LP 102 is shown as including a magnetic field sensor 156. The magnetic field sensor 156 can be, e.g., a Hall effect sensor, that is capable of detecting the relatively large static magnetic fields produced by MRI systems. The magnetic field sensor 156 can alternatively be a giant magnetoresistance (GMR) sensor, or a reed switch, but is not limited thereto. In accordance with certain embodiments of the present technology, the magnetic field sensor 156 is used to detect when the LP 102 (or some other type of IMD) is being exposed to a magnetic field that is likely generated by an MRI system, and based thereon, the LP 102 (or other type of IMD) can automatically switch one or more of its modes of operation. This can include switching its pacing mode, e.g., from a DOO mode to a VOO mode, but is not limited thereto. This can additionally, or alternatively, include switching is a mode of communication, e.g., from using only a conductive communication mode, to using an RF communication mode alone or together with the conductive communication mode, as will be explained in additional detail below.

Instead of, or in addition to, using the magnetic field sensor 156 to detect a magnetic field for the purpose of determining when the LP 102 (or other type of IMD) is likely being exposed to an MRI system, another type of sensor can be used to detect a surrogate of a magnetic field that is produced by an MRI system. Such a surrogate of a magnetic field that is produced by an MRI system can be a secondary acoustic and/or vibratory effect of an MRI system. More specifically, the accelerometer 143 (or some other sensor configured to detect acceleration, sound and/or vibration), while not capable of actually detecting the magnetic field from an MRI system, can detect secondary acoustic and/or vibratory effects of an MRI system. That is, while an intended purpose of an MRI system is to generate time-varying gradient magnetic fields, unintended but inevitable results of generating the time-varying gradient magnetic fields are relatively loud noises and vibrations, which are surrogates of the magnetic field generated by the MRI system. Certain embodiments of the present technology take advantage of such unintended but inevitable secondary acoustic and/or vibratory effects of an MRI system.

In various embodiments, LP 102a, 102b can manage power consumption to draw limited power from the battery, thereby reducing device volume. Each circuit in the system can be designed to avoid large peak currents. For example, cardiac pacing can be achieved by discharging a tank capacitor (not shown) across the pacing electrodes. Recharging of the tank capacitor is typically controlled by a charge pump circuit. In a particular embodiment, the charge pump circuit is throttled to recharge the tank capacitor at constant power from the battery.

In some embodiments, the controller 112 in an LP 102 can access signals on the electrodes 108 and can examine output pulse duration from another LP 102 for usage as a signature for determining triggering information validity and, for a signature arriving within predetermined limits, activating delivery of a pacing pulse following a predetermined delay of zero or more milliseconds. The predetermined delay can be preset at manufacture, programmed via an external programmer, or determined by adaptive monitoring to facilitate recognition of the triggering signal and discriminating the triggering signal from noise. In some embodiments or in some conditions, the controller 112 can examine output pulse waveform from another leadless cardiac pacemaker for usage as a signature for determining triggering information validity and, for a signature arriving within predetermined limits, activating delivery of a pacing pulse following a predetermined delay of zero or more milliseconds.

Figure 3:
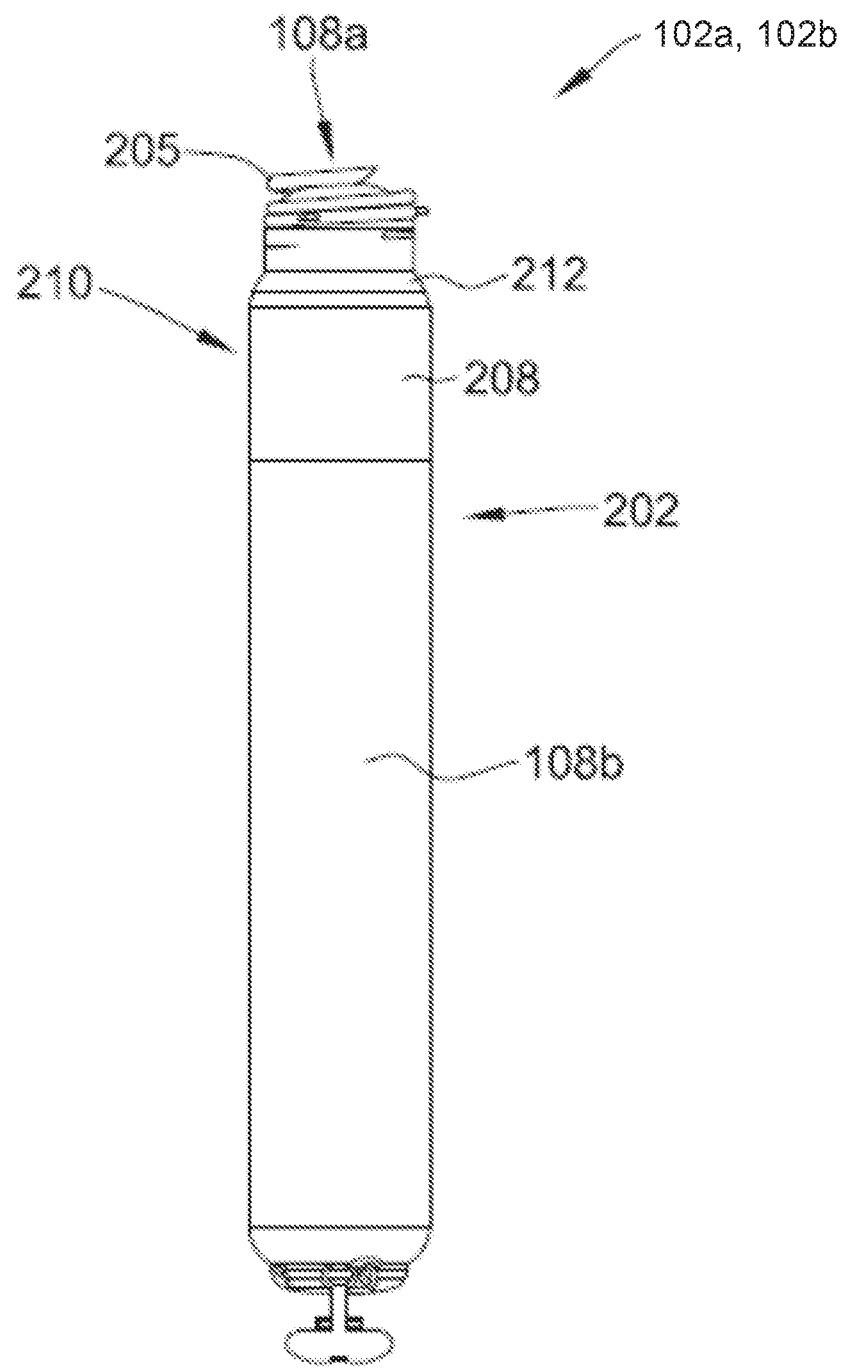
FIG. 3 illustrates an LP in accordance with certain embodiments herein.

FIG. 3 shows an example form factor of the LPs 102a, 102b. Each LP can include a hermetic housing 202 (e.g., 110 in FIG. 2) with electrodes 108a and 108b disposed thereon. As shown, electrode 108a can be separated from but surrounded partially by a fixation mechanism 205, and the electrode 108b can be disposed on the housing 202. The fixation mechanism 205 can be a fixation helix, a plurality of hooks, barbs, or other attaching features configured to attach the pacemaker to tissue, such as heart tissue. As noted above, an antenna (e.g., 118) can be at least partially implanted by or as part of the fixation mechanism. The electrodes 108a and 108b are examples of the electrodes 108 shown in and discussed above with reference to FIG. 2.

The housing can also include an electronics compartment 210 within the housing that contains the electronic components necessary for operation of the pacemaker, including, e.g., a pulse generator, transceiver, a battery, and a processor for operation. The hermetic housing 202 can be adapted to be implanted on or in a human heart, and can be cylindrically shaped, rectangular, spherical, or any other appropriate shapes, for example.

The housing can comprise a conductive, biocompatible, inert, and anodically safe material such as titanium, 316L stainless steel, or other similar materials. The housing can further comprise an insulator disposed on the conductive material to separate electrodes 108a and 108b. The insulator can be an insulative coating on a portion of the housing between the electrodes, and can comprise materials such as silicone, polyurethane, parylene, or another biocompatible electrical insulator commonly used for implantable medical devices. In the embodiment of FIG. 2, a single insulator 208 is disposed along the portion of the housing between electrodes 108a and 108b. In some embodiments, the housing itself can comprise an insulator instead of a conductor, such as an alumina ceramic or other similar materials, and the electrodes can be disposed upon the housing.

As shown in FIG. 3, the pacemaker can further include a header assembly 212 to isolate 108a and 108b. The header assembly 212 can be made from PEEK, tecothane or another biocompatible plastic, and can contain a ceramic to metal feedthrough, a glass to metal feedthrough, or other appropriate feedthrough insulator as known in the art.

The electrodes 108a and 108b can comprise pace/sense electrodes, or return electrodes. A low-polarization coating can be applied to the electrodes, such as sintered platinum, platinum-iridium, iridium, iridium-oxide, titanium-nitride, carbon, or other materials commonly used to reduce polarization effects, for example. In FIG. 2, electrode 108a can be a pace/sense electrode and electrode 108b can be a return electrode. The electrode 108b can be a portion of the conductive housing 202 that does not include an insulator 208.

Several techniques and structures can be used for attaching the housing 202 to the interior or exterior wall of the heart. A helical fixation mechanism 205, can enable insertion of the device endocardially or epicardially through a guiding catheter. A torqueable catheter can be used to rotate the housing and force the fixation device into heart tissue, thus affixing the fixation device (and also the electrode 108a in FIG. 2) into contact with stimulable tissue. Electrode 108b can serve as an indifferent electrode for sensing and pacing. The fixation mechanism may be coated partially or in full for electrical insulation, and a steroid-eluting matrix may be included on or near the device to minimize fibrotic reaction, as is known in conventional pacing electrode-leads.

Implant-to-Implant Event Messaging

LPs 102a and 102b can utilize implant-to-implant (i2i) communication through event messages to coordinate operation with one another in various manners. The terms i2i communication, i2i event messages, and i2i event markers are used interchangeably herein to refer to event related messages and IMD/IMD operation related messages transmitted from an implanted device and directed to another implanted device (although external devices, e.g., a programmer, may also receive i2i event messages). In certain embodiments, LP 102a and LP 102b operate as two independent leadless pacers maintaining beat-to-beat dual-chamber functionality via a "Master/Slave" operational configuration. For descriptive purposes, the ventricular LP 102b shall often be referred to as "vLP" and the atrial LP 102a shall often be referred to as "aLP". The LP 102 that is designated as the master device (e.g., vLP) may implement all or most dual-chamber diagnostic and therapy determination algorithms. For purposes of the following illustration, it is assumed that the vLP is a "master" device, while the aLP is a "slave" device. Alternatively, the aLP may be designated as the master device, while the vLP may be designated as the slave device. The master device orchestrates most or all decision-making and timing determinations (including, for example, rate-response changes).

In accordance with certain embodiments, methods are provided for coordinating operation between first and second leadless pacemakers (LPs) configured to be implanted entirely within first and second chambers of the heart. A method transmits an event marker through conductive communication through electrodes located along a housing of the first LP, the event marker indicative of one of a local paced or sensed event. The method detects, over a sensing channel, the event marker at the second LP. The method identifies the event marker at the second LP based on a predetermined pattern configured to indicate that an event of interest has occurred in a remote chamber. In response to the identifying operation, the method initiates a related action in the second LP. In certain embodiments, event messages and/or other types of i2i messages can be alternatively, or additionally, transmitted using RF communication, as will be described in more detail below.

Figure 4:
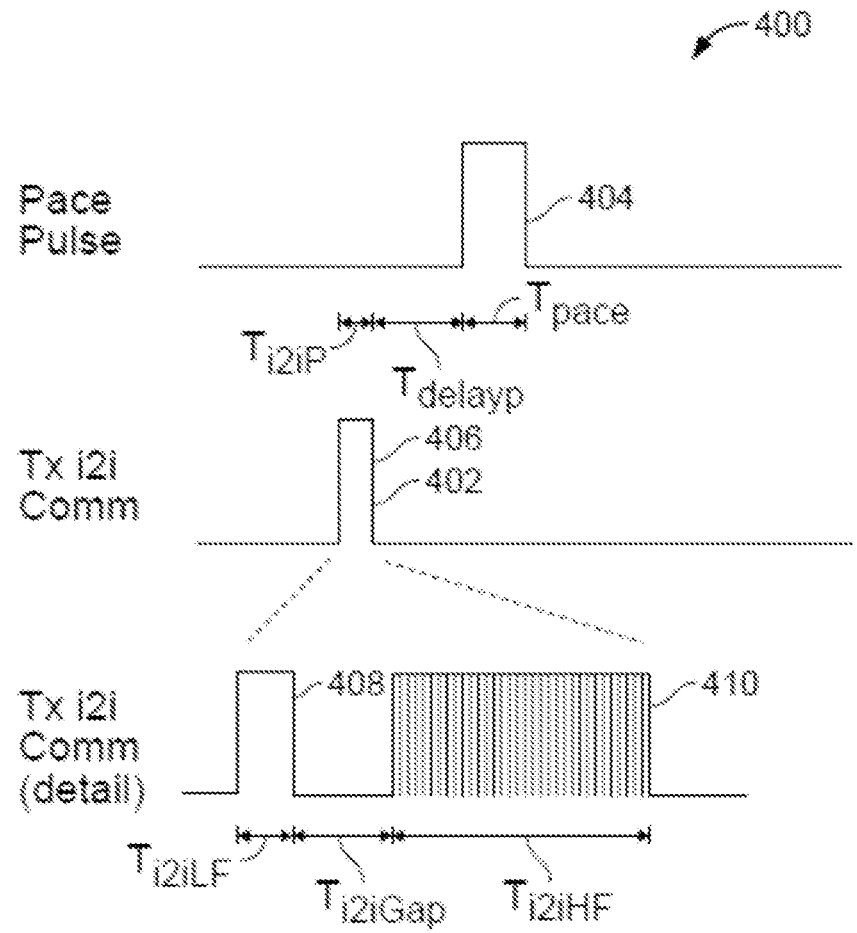
FIG. 4 is a timing diagram demonstrating one embodiment of i2i communication for a paced event.

FIG. 4 is a timing diagram 400 demonstrating one example of an i2i conductive communication for a paced event. The i2i conductive communication may be transmitted, for example, from LP 102a to LP 102b. As shown in FIG. 4, in this embodiment, an i2i transmission 402 is sent prior to delivery of a pace pulse 404 by the transmitting LP (e.g., LP 102a). This enables the receiving LP (e.g., LP 102b) to prepare for the remote delivery of the pace pulse. The i2i transmission 402 includes an envelope 406 that may include one or more individual pulses. For example, in this embodiment, envelope 406 includes a low frequency pulse 408 followed by a high frequency pulse train 410. Low frequency pulse 408 lasts for a period $T_{i2iLF}$, and high frequency pulse train 410 lasts for a period $T_{i2iHF}$. The end of the low frequency pulse 408 and the beginning of the high frequency pulse train 410 are separated by a gap period, $T_{i2iGap}$. In alternative embodiments, rather than transmitting the envelope 406 prior to the pacing pulse 404, the envelope 406 can be transmitted during a refractory period that follows the delivery of the pacing pulse.

As shown in FIG. 4, the i2i transmission 402 lasts for a period Ti2iP, and pace pulse 404 lasts for a period Tpace. The end of i2i transmission 402 and the beginning of pace pulse 404 are separated by a delay period, TdelayP. The delay period may be, for example, between approximately 0.0 and 10.0 milliseconds (ms), particularly between approximately 0.1 ms and 2.0 ms, and more particularly approximately 1.0 ms. The term approximately, as used herein, means +/−10% of a specified value.

Figure 5:
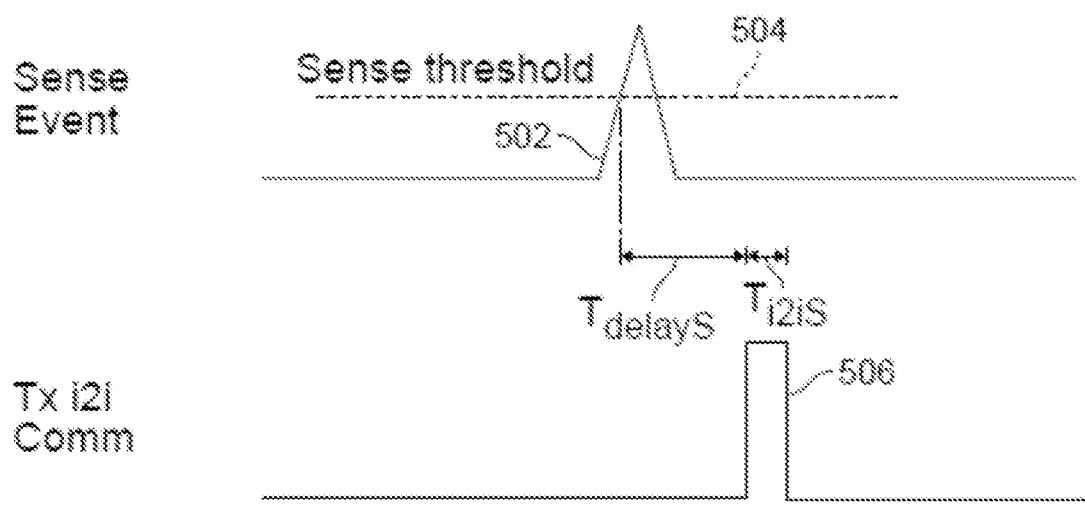
FIG. 5 is a timing diagram demonstrating one embodiment of i2i communication for a sensed event.

FIG. 5 is a timing diagram 500 demonstrating one example of an i2i communication for a sensed event. The i2i communication may be transmitted, for example, from LP 102a to LP 102b. As shown in FIG. 5, in this embodiment, the transmitting LP (e.g., LP 102a detects the sensed event when a sensed intrinsic activation 502 crosses a sense threshold 504. A predetermined delay period, $T_{delayS}$, after the detection, the transmitting LP transmits an i2i transmission 506 that lasts a predetermined period $T_{i2iS}$. The delay period may be, for example, between approximately 0.0 and 10.0 milliseconds (ms), particularly between approximately 0.1 ms and 2.0 ms, and more particularly approximately 1.0 ms.

As with i2i transmission 402, i2i transmission 506 may include an envelope that may include one or more individual pulses. For example, similar to envelope 406, the envelope of i2i transmission 506 may include a low frequency pulse followed by a high frequency pulse train. In certain embodiments, the i2i transmission 506 is transmitted during a refractory period that follows the sensed event.

Optionally, wherein the first LP is located in an atrium and the second LP is located in a ventricle, the first LP produces an AS/AP event marker to indicate that an atrial sensed (AS) event or atrial paced (AP) event has occurred or will occur in the immediate future. For example, the AS and AP event markers may be transmitted following the corresponding AS or AP event. Alternatively, the first LP may transmit the AP event marker slightly prior to delivering an atrial pacing pulse. Alternatively, wherein the first LP is located in an atrium and the second LP is located in a ventricle, the second LP initiates an atrioventricular (AV) interval after receiving an AS or AP event marker from the first LP; and initiates a post atrial ventricular blanking (PAVB) interval after receiving an AP event marker from the first LP.

Optionally, the first and second LPs may operate in a "pure" master/slave relation, where the master LP delivers "command" markers in addition to or in place of "event" markers. A command marker directs the slave LP to perform an action such as to deliver a pacing pulse and the like. For example, when a slave LP is located in an atrium and a master LP is located in a ventricle, in a pure master/slave relation, the slave LP delivers an immediate pacing pulse to the atrium when receiving an AP command marker from the master LP.

In accordance with some embodiments, communication and synchronization between the aLP and vLP is implemented via conducted communication of markers/commands in the event messages (per i2i communication protocol). As explained above, conducted communication represents event messages transmitted from the sensing/pacing electrodes at frequencies outside the RF (e.g., Wi-Fi or BLE) frequency range. Alternatively, the event messages may be conveyed over communication channels operating in the RF frequency range. The figures and corresponding description below illustrate non-limiting examples of markers that may be transmitted in event messages. The figures and corresponding description below also include the description of the markers and examples of results that occur in the LP that receives the event message. Table 1 represents example event markers sent from the aLP to the vLP, while Table 2 represents example event markers sent from the vLP to the aLP. In the master/slave configuration, AS event markers are sent from the aLP each time that an atrial event is sensed outside of the post ventricular atrial blanking (PVAB) interval or some other alternatively-defined atrial blanking period. The AP event markers are sent from the aLP each time that the aLP delivers a pacing pulse in the atrium. The aLP may restrict transmission of AS markers, whereby the aLP transmits AS event markers when atrial events are sensed both outside of the PVAB interval and outside the post ventricular atrial refractory period (PVARP) or some other alternatively-defined atrial refractory period. Alternatively, the aLP may not restrict transmission of AS event markers based on the PVARP, but instead transmit the AS event marker every time an atrial event is sensed.

TABLE 1

"A2V" Markers/Commands (i.e., from aLP to vLP)

| Marker | Description | Result in vLP |
|---|---|---|
| AS | Notification of a sensed event in atrium (if not in PVAB or PVARP) | Initiate AV interval (if not in PVAB or PVARP) |

TABLE 1-continued

"A2V" Markers/Commands (i.e., from aLP to vLP)

| Marker | Description | Result in vLP |
|---|---|---|
| AP | Notification of a paced event in atrium | Initiate PAVB<br>Initiate AV interval (if not in PVARP) |

As shown in Table 1, when an aLP transmits an event message that includes an AS event marker (indicating that the aLP sensed an intrinsic atrial event), the vLP initiates an AV interval timer. If the aLP transmits an AS event marker for all sensed events, then the vLP would preferably first determine that a PVAB or PVARP interval is not active before initiating an AV interval timer. If however the aLP transmits an AS event marker only when an intrinsic signal is sensed outside of a PVAB or PVARP interval, then the vLP could initiate the AV interval timer upon receiving an AS event marker without first checking the PVAB or PVARP status. When the aLP transmits an AP event marker (indicating that the aLP delivered or is about to deliver a pace pulse to the atrium), the vLP initiates a PVAB timer and an AV interval time, provided that a PVARP interval is not active. The vLP may also blank its sense amplifiers to prevent possible crosstalk sensing of the remote pace pulse delivered by the aLP.

TABLE 2

"V2A" Markers/Commands (i.e., from vLP to aLP)

| Marker | Description | Result in aLP |
|---|---|---|
| VS | Notification of a sensed event in ventricle | Initiate PVARP |
| VP | Notification of a paced event in ventricle | Initiate PVAB<br>Initiate PVARP |
| AP | Command to deliver immediate pace pulse in atrium | Deliver immediate pace pulse to atrium |

As shown in Table 2, when the vLP senses a ventricular event, the vLP transmits an event message including a VS event marker, in response to which the aLP may initiate a PVARP interval timer. When the vLP delivers or is about to deliver a pace pulse in the ventricle, the vLP transmits VP event marker. When the aLP receives the VP event marker, the aLP initiates the PVAB interval timer and also the PVARP interval timer. The aLP may also blank its sense amplifiers to prevent possible crosstalk sensing of the remote pace pulse delivered by the vLP. The vLP may also transmit an event message containing an AP command marker to command the aLP to deliver an immediate pacing pulse in the atrium upon receipt of the command without delay.

The foregoing event markers are examples of a subset of markers that may be used to enable the aLP and vLP to maintain full dual chamber functionality. In one embodiment, the vLP may perform all dual-chamber algorithms, while the aLP may perform atrial-based hardware-related functions, such as PVAB, implemented locally within the aLP. In this embodiment, the aLP is effectively treated as a remote 'wireless' atrial pace/sense electrode. In another embodiment, the vLP may perform most but not all dual-chamber algorithms, while the aLP may perform a subset of diagnostic and therapeutic algorithms. In an alternative embodiment, vLP and aLP may equally perform diagnostic and therapeutic algorithms. In certain embodiments, decision responsibilities may be partitioned separately to one of the aLP or vLP. In other embodiments, decision responsibilities may involve joint inputs and responsibilities.

Messages that are transmitted between LPs (e.g., the aLP and the vLP) can be referred to herein generally as i2i messages, since they are implant-to-implant messages. As noted above, such messages can include event markers that enable one LP to inform the other LP of a paced event or a sensed event. For example, in certain embodiments, whenever the aLP 102a senses an atrial event or paces the right atrium, the aLP will transmit an i2i message to the vLP 102b to inform the vLP of the sensed or paced event in the atrium. In response to receiving such an i2i message, the vLP 102b may start one or more timers that enable the vLP to sense or pace in the right ventricle. Similarly, the vLP may transmit an i2i message to the aLP 102a whenever the vLP senses a ventricular event or paces the right ventricle.

The i2i messages that are sent between LPs may be relatively short messages that simply allow a first LP to inform a second LP of an event that was sensed by the first LP or caused (paced) by the first LP, and vice versa. Such i2i messages can be referred to herein as event marker i2i messages, or more succinctly as event i2i messages. The i2i messages that are sent between LPs, in certain instances, can be extended i2i messages that include (in addition to an event marker) an extension. In certain embodiments, an extended i2i message includes an event marker (e.g., 9 bits), followed by an extension indicator (e.g., 2 bits), followed by an extended message payload portion (e.g., 17 bits), followed by a cyclic redundancy check (CRC) code (e.g., 6 bits) or some other type of error detection and correction code.

In certain embodiments, whenever an i2i message is sent by an LP (or other type of IMD, such as a S-ICD), the i2i message will include an extension indicator so that the receiving LP knows whether or not the i2i message it receives includes an extension portion. In such embodiments, even a relatively short event i2i message will include an extension indicator. The extension indicator (e.g., 2 bits) is used by the LP (or other IMD) sending the i2i message to indicate, to the LP receiving the i2i message, whether or not the i2i message is an extended i2i message. In certain embodiments, if the LP receiving an i2i message determines based on the extension indicator bits that the received i2i message is not an extended i2i message, then the LP receiving the i2i message can ignore any bits that follow the extension bits. In such a case, the LP receiving the i2i message only decodes the event marker. On the other hand, if the LP receiving an i2i message determines based on the extension indicator bits that the received i2i message is an extended i2i message, then the LP receiving the i2i message will also decode the bits that follow the extension bits, and determine based on a CRC code (or other type of error detection and correction code), whether the i2i message is a valid message. If the extended i2i message is a valid i2i message, then the LP receiving the extended i2i message will as appropriate modify its operation, update parameters, and/or the like, based on information included in the extended i2i message. In certain embodiments, event i2i messages that are not extended i2i messages do not include any error detection and correction code.

In an extended i2i message, the event marker bits and the extension indicator bits are located, respectively, in an event marker field and an extension indicator field of an i2i message packet. In certain embodiments, the extended portion (that follows the event marker bits and the extension indicator bits) includes message bits (in a message field) and rate indicator bits (in a rate indicator field), which are parts of the payload. The payload can alternatively, or additionally, include other types of fields, such as an acknowledgement field that is used in certain situations for one LP to acknowledge reception of an i2i message from another LP of certain (e.g., critical) types of message.

More generally, various different types of information may be included within the payload of an extended i2i message. For one example, the payload can include a pacing rate indicator that enables one LP to inform another LP of a pacing rate. For example, assume that an LP system provides rate responsive pacing, wherein a pacing rate is adjusted in dependence on a patient's physical activity as detected, e.g., using an accelerometer, temperature sensor, and/or other type of sensor of an LP. In such an LP system, the vLP may inform the aLP of the rate at which the patient's heart should be paced so that the aLP and vLP can perform synchronized pacing. To achieve this, the vLP can send a pacing rate indicator to the aLP in the payload of an extended i2i message. The pacing rate indicator can, e.g., be a value indicating a pacing rate value (e.g., 80 bpm), a code that the aLP that can look up (e.g., in a stored look up table) and corresponds to a pacing rate value, or a value that the aLP feeds into an equation to determine the pacing rate, but is not limited thereto. Alternatively, the pacing rate indicator can be beat-to-beat interval value (e.g., 0.75 seconds), a code that the aLP can look up and corresponds to a beat-to-beat interval value, or a value that the aLP feeds into an equation to determine the beat-to-beat interval, but is not limited thereto. Other variations are also possible and within the scope of the embodiments described herein.

Selective Use of RF Communication

As noted above, implantable medical devices and systems often rely on proper i2i communication to operate correctly. For example, in a dual leadless pacemaker system, such as the one described above with reference to FIGS. 1-5, i2i communication is critical for proper synchronization of the system. However, where i2i communication is performed using conductive communication, there may be situations where i2i communication is unreliable or simply fails, which adversely affects the ability of the system to perform synchronous pacing. For example, when a patient having two LPs undergoes an MRI scan that is performed by an MRI system, the gradient noise produced by the MRI system will prevent the LPs from successfully communicating with one another using conductive communication. For a more specific example, where a patient has two implanted LPs that rely on conductive communication to perform synchronous dual chamber pacing (e.g., DOO mode pacing), the ability to perform synchronous dual chamber pacing would breakdown when the patient is subjected to an MRI scan. The conventional thinking is that such a dual chamber LP system should be switched from a dual chamber pacing mode (e.g., DOO mode pacing) to a single chamber pacing mode (e.g., VOO mode pacing) prior to an MRI scan using an external programmer (e.g., 109). Alternatively, the LPs 102 can use a sensor to detect when they are being subjected to an MRI scan, and in response thereto the LPs 102 can autonomously switch themselves to a single chamber pacing mode (e.g., VOO mode pacing). Thereafter, when the LPs 102 no longer detect that they are being subjected to an MRI scan, the LPs 102 can autonomously switch themselves back to the dual chamber pacing mode. However, while the patient is being paced in accordance with the single chamber pacing mode (e.g., VOO mode pacing), the patient may not receive the appropriate level of care that the patient needs, which is undesirable.

Because the frequencies used for RF communication are above the frequencies produced by an MRI system, IMDs can communicate with one another using RF communication even when the IMDs are subjected to an MRI scan. However, a detriment of IMDs only utilizing RF communication to communicate with one another is that RF communication is much less power efficient than conductive communication, rendering the lifespan of such IMDs relatively short of the IMD only used RF communication to communicate with another IMD, which is undesirable.

In accordance with certain embodiments of the present technology, IMDs (e.g., such as two LPs of a dual chamber LP system) are configured to communicate with one another primarily and by default using conductive communication, which is energy efficient, and the IMDs are configured to use RF communication (which is less energy efficient) as a backup up and/or auxiliary type of communication. With such embodiments, the lifespan of the IMDs can be relatively long, potentially up to seven years or more, which is desirable. There are various different ways that such embodiments can be achieved, as will be described below. However, in order for these embodiments to be implemented, the IMDs should be capable of performing both conductive communication and RF communication. The LPs 102, described above with reference to FIGS. 1-5, are examples of IMDs that are capable of performing both conductive communication and RF communication, because they include by a conducive communication transceiver and an RF communication transceiver. However, embodiments of the present technology are not just limited to use with the LPs 102 described herein, as would be appreciated by one of ordinary skill in the art reading this document.

In accordance with certain embodiments, IMDs (e.g., LPs 102) are configured to normally communicate with one another using conductive communication (and more specifically, by sending conductive communication messages to one another), while an MRI mode of the IMD is deactivated (aka turned off), and the IMDs are configured to communicate with one another using RF communication (and more specifically, by sending RF communication messages to one another) when the MRI mode of the IMD is activated (aka turned on). This is beneficial because the IMDs will normally communicate using energy efficient conductive communication, and the IMDs will still be able to communicate with one another (albeit less energy efficiently) using RF communication when the IMDs are subjected to an MRI scan. In certain such embodiments, the MRI mode of the IMDs can be selectively activated (i.e., turned on) using a non-implanted device, such as, but not limited to, an external programmer (e.g., 109) that wirelessly communicates with the IMD. Once the MRI mode of the IMDs is activated, the MRI mode of the IMDs can be deactivated (e.g., after an MRI scan is completed) by the same non-implanted device, or another non-implanted device. It would also be possible for the MRI mode to be deactivated (i.e., turned off) after a specified amount of time has elapsed since the MRI mode was turned on. In other words, a controller 112 and/or timer of an IMD can be used to determine whether an MRI timeout period (e.g., 6 hours) has expired, and the IMD can be autonomously deactivate (i.e., turn off) that MRI mode once the MRI timeout period expires. This way, if a clinician forgets to use a programmer (or some other type of non-implanted device) to turn off the MRI mode of an IMD, the IMD will not be stuck in the MRI mode indefinitely. It is noted that the terms active, enable, and turn on, are often used interchangeably herein. Similarly, the terms deactivate, disable, and turn off, or often used interchangeably herein.

Depending upon the specific implementation, the MRI mode of an IMD can cause the IMD to send messages using RF communication instead or, or in addition to, sending messages using conductive communication. In other words, when an IMD is in its IMD mode, the IMD can transmit just RF communication messages to another IMD, or the IMD can transmit both RF communication messages and conductive communication messages. In accordance with certain embodiments, the RF communication transceiver (e.g., 134) of an IMD (e.g., LP 102) is disabled when the MRI mode is deactivated, and the RF communication transceiver is enabled when the MRI mode is activated. In certain embodiments, at least a portion of the conductive communication transceiver (e.g., 124) is disabled when the RF communication transceiver (e.g., 134) is enabled. For example, the receiver(s) (e.g., 120, 124) of the conductive communication transceiver can be disabled while the RF communication transceiver is enabled. In other embodiments, the conductive communication transceiver (e.g., 124) remains enabled while the RF communication transceiver (e.g., 134) is enabled, so that a controller (e.g., 112) of the IMD can determine when a conductive communication capability has been restored, in response to which, the RF communication transceiver (e.g., 134) can be disabled.

There can be additional components and/or capabilities of an IMD (e.g., LP 102) that can be selectively enabled and disabled based on whether or not the IMD is in its MRI mode. However, in certain embodiments, the components and/or capabilities of an IMD that are selectively enabled and disabled, based on whether or not the IMD is in its MRI mode, only involve communication components and capabilities of the IMD. More specifically, in certain embodiments conductive communication capabilities are enabled and RF communication capabilities are disabled when the MRI mode is turned off, and RF communication capabilities are enabled when the MRI mode is turned on. In certain such embodiments, when the MRI mode is turned on, the conductive communication capabilities are disabled. In other embodiments, when the MRI mode is turned on, the conductive communication capabilities remain enabled, such that when the MRI mode it turned on, both the RF communication and the conductive communication capabilities of the IMD are enabled.

In certain embodiments, rather than relying on a clinician to use a non-implanted device (e.g., a programmer 109) to activate and deactivate an MRI mode of IMDs (e.g., LPs 102), the IMDs can themselves detect when the IMDs are likely being exposed to an MRI scan, and the IMDs themselves can selectively activate their MRI mode. More specifically, a sensor of an IMD can detect a magnetic field, or a surrogate thereof, that is likely generated by an MRI system, and in response thereto, the IMD (or more specifically, the controller thereof) can activate the MRI mode of the IMD. For example, referring back to FIG. 2, the magnetic field sensor 156 can be used to detect when the LP 102 is being exposed to a magnetic field that is likely generated by an MRI system. Such a sensor can be, e.g., a Hall effect sensor, a GMR sensor, or a reed switch, but is not limited thereto, as explained above. Instead of, or in addition to, using a magnetic field sensor (e.g., 156) to detect a magnetic field for the purpose of determining when the LP 102 (or other type of IMD) is likely being exposed to an MRI system, another type of sensor can be used to detect a surrogate of a magnetic field that is produced by an MRI system, which in response to be detected, causes an MRI mode of the LP 102 to be activated. Such a surrogate of a magnetic field that is produced by an MRI system can be a secondary acoustic and/or vibratory effect of an MRI system. More specifically, the accelerometer 143 (or some other sensor configured to detect acceleration, sound and/or vibration) of the LP 102, while not capable of actually detecting the magnetic field from an MRI system, can detect secondary acoustic and/or vibratory effects of an MRI system, as was described above, which in response to be detected, can cause an MRI mode of the LP 102 to be activated.

Certain embodiments of the present technology, where are described below, related to systems, methods, and devices for improving communication between first and second IMDs, wherein such IMDs are remotely located relative to one another and are capable of communicating with one another using both conductive communication and RF communication. Referring briefly back to FIG. 1, the first and second IMDs can be the LPs 102a and 102b, respectively. Alternatively, the first and second IMDs can be the LPs 102b and 102a, respectively. In other embodiments, the first IMD can be one of the LPs 102a or 102b, and the second IMD can be the S-ICD 106. In still other embodiments, the first IMD can be the S-ICD 106, and the second IMD can be one of the LPs 102a or 102b. It would also be possible that one of the first and second IMDs is an insertable cardiac monitor (ICM). One of the first and second IMDs can be a non-vascular implantable cardioverter-defibrillator (NV-ICD), e.g., 106, which may or may not be an S-ICD. These are just a few examples of the types of IMDs with which embodiments of the present technology can be used, which examples are not intended to be all encompassing.

Figure 6A:
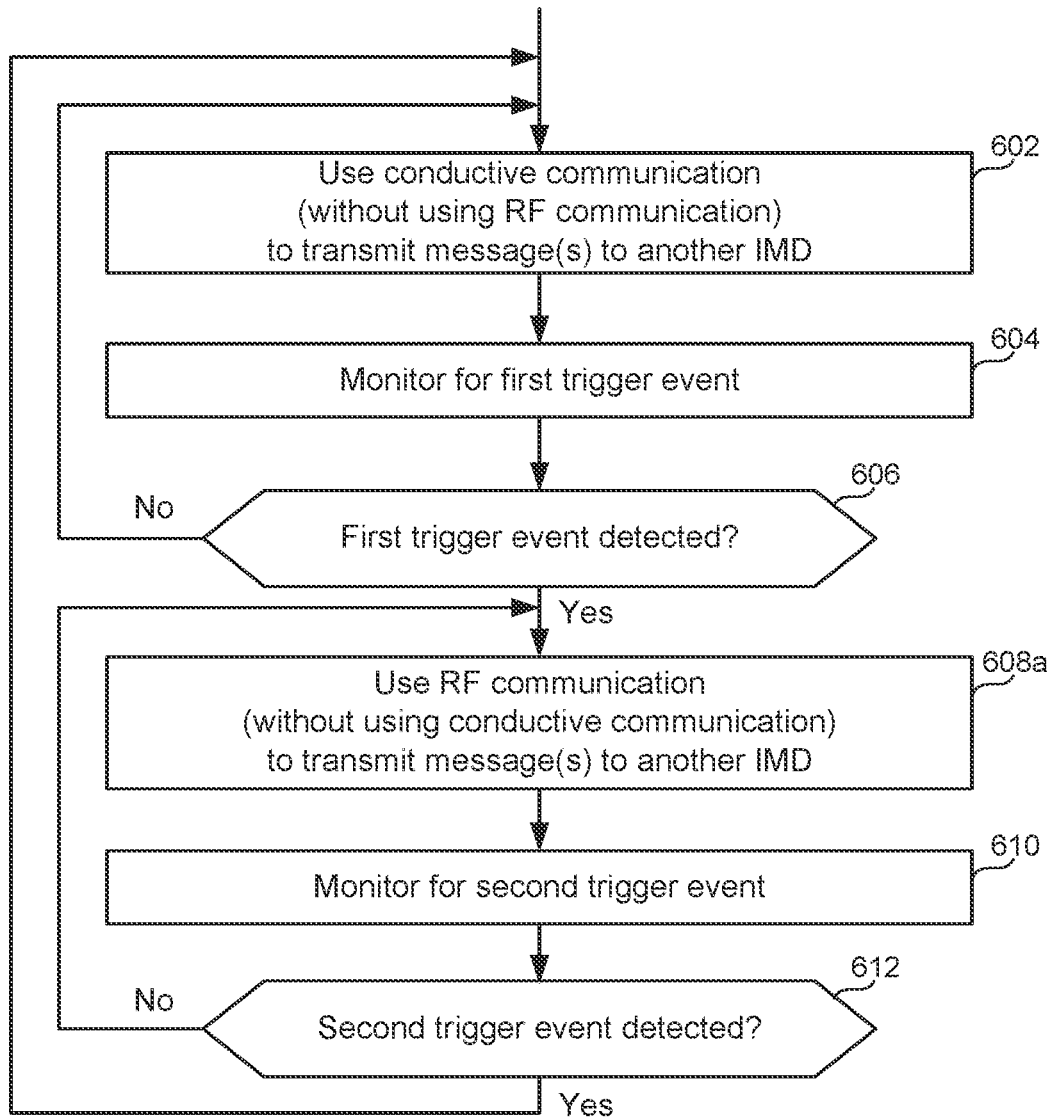
FIG. 6A is a high level flow diagram that is used to summarize methods for improving communication between IMDs, according to certain embodiments of the present technology.

FIG. 6A is a high level flow diagram that is used to summarize methods for improving communication between first and second IMDs, wherein such IMDs are remotely located relative to one another and are capable of communicating with one another using both conductive communication and RF communication, according to certain embodiments of the present technology. The steps shown in FIG. 6A are from the perspective of the first IMD, and are performed by the first IMD. The second IMD can independently perform the same or similar steps, in which case from the perspective of the second IMD the terms first and second can be swapped in FIG. 6A (and similarly, in FIG. 6B).

Referring to FIG. 6A, step 602 involves the first IMD using conductive communication to transmit one or more messages intended for the second IMD, without using RF communication to transmit any messages intended for the second IMD. In accordance with certain embodiments, the first IMD can be configured to normally and/or by default use conductive communication as its primary and preferred mode of communication, because conductive communication is significantly more energy efficient than RF communication. Where the first IMD is an LP, such as the aLP 102a or the vLP 102b, and the second IMD is the other one of the LPs 102a, 102b, the messages that are sent from the first IMD to the second IMD can be an i2i message that informs the second IMD of an intrinsic or paced cardiac event that occurred in a first cardiac chamber (in or on which the first IMD is implanted), so that the second IMD can appropriate time its pacing of a second cardiac chamber (in or on which the second IMD is implanted). More generally, such messages can be event messages, but are not limited thereto.

For more specific examples, where the first IMD is the aLP 102a and the second IMD is the vLP 102b, at step 602 the messages that are sent by the aLP 102a to the vLP 102b using conductive communication can be or include an atrial sensed (AS) event marker, or an atrial paced (AP) event marker, or can include some other type of message, such as a command message, or an acknowledgement (ACK) message that the aLP 102*a* uses to acknowledge that it received a message from the vLP 102*b*. Where the first IMD is the vLP 102*b* and the second IMD is the aLP 102*a*, the messages that are sent by the vLP 102*b* to the aLP 102*a* can be or include a ventricular sensed (VS) event marker, or a ventricular paced (VP) event marker, or can include some other type of message, such as a command message, or an acknowledgement (ACK) message that the vLP 102*b* uses to acknowledge that it received a message from the aLP 102*a*. These are just a few examples of the types of messages that can be sent from a first IMD to a second IMD, and vice versa, which are not intended to be all encompassing. Indeed, as explained above, one or both the IMDs need not be an LP. However, for the remainder of this discussion, it is often assumed that the first and second IMDs are LPs.

Still referring to FIG. 6A, step 604 involves monitoring for a first trigger event, and step 606 involves determining whether the first trigger event was detected. While steps 604 and 606 are shown as separate steps in FIG. 6A, it would also be possible that steps 604 and 606 be combined into a single step. The first trigger event that is monitored for at steps 604 and 606, as will be appreciated from the discussion below, is some type of event that would adversely affect the efficacy of conductive communication, such that the first IMD should start using RF communication (at least temporarily) instead of (or in addition to) using conductive communication to send message(s) to the second IMD, even though RF communication is less energy efficient than conductive communication.

If the answer to the determination at step 606 is No (i.e., if the first trigger event is not detected), then flow returns to step 602 and the first IMD continues to use conductive communication (without using RF communication) to transmit message(s) to the second IMD. In other words, steps 602, 604, and 606 will continue in a loop until the answer to the determination at step 606 is Yes. The period of time during which the first IMD transmits messages to the second IMD using conductive communication, without using RF communication, can be referred to herein as a first period of time.

If the answer to the determination at step 606 is Yes (i.e., if the first trigger event is detected), then flow goes to step 608*a* and the first IMD starts using RF communication (without using conductive communication) to transmit message(s) to the second IMD.

Still referring to FIG. 6A, step 610 involves monitoring for a second trigger event, and step 612 involves determining whether the second trigger event was detected. While steps 610 and 612 are shown as separate steps in FIG. 6A, it would also be possible that steps 610 and 612 be combined into a single step. The second trigger event that is monitored for at steps 610 and 612, as will be appreciated from the discussion below, is some type of event that would favorably affect the efficacy of conductive communication, such that the first IMD should return to using conductive communication instead of using RF communication to send message(s) to the second IMD, because conductive communication is more energy efficient than RF communication.

If the answer to the determination at step 612 is No (i.e., if the second trigger event is not detected), then flow returns to step 608*a* and the first IMD continues to use RF communication (without using conductive communication) to transmit message(s) to the second IMD. In other words, steps 608*a*, 610, and 612 will continue in a loop until the answer to the determination at step 612 is Yes. The period of time during which the first IMD transmits messages to the second IMD using RF communication, can be referred to herein as a second period of time.

If the answer to the determination at step 612 is Yes (i.e., if the second trigger event is detected), then flow goes to back to step 602 and the first IMD starts using conductive communication (without using RF communication) to transmit message(s) to the second IMD.

The messages that the first IMD transmits to the second IMD at instances of steps 602 and 604 can also be referred to as messages intended for the second IMD, since the second IMD is the intended recipient of the messages, but there is no guarantee that the messages will actually be received by the second IMD. In accordance with certain embodiments, the one or more messages intended for the second IMD, that are transmitted by the first IMD using conductive communication at one or more instances of step 602 during the first period of time, are transmitted within a first frequency range. By contrast, the one or more messages intended for the second IMD, that are transmitted by the first IMD using RF communication during the second period of time, are transmitted within a second frequency range that is above the first frequency range. For example, the frequency range that is used for performing conductive communication at instances of step 602 can be, e.g., within the range of about 1 KHz to about 250 KHz. By contrast, the frequency range that is used for RF communication at instances of step 608*a* is significantly higher, depending upon which type of RF communication is used. For example, if Bluetooth Low Energy (BLE) is used for RF communication at instance of step 608*a*, then the frequency range is within the range of about 2.40 GHz to about 2.48 GHz. For another example, if the Medical Device Radiocommunications Service (MedRadio) is used for RF communication at instances of step 608*a*, then the frequency range is within the range of about 400 MHz to about 406 MHz. It would also be possible to use one of the WiFi frequency bands for RF communication.

In accordance with certain embodiments, the first trigger event that is monitored for (at steps 604 and/or 606) comprises a magnetic resonance imaging (MRI) mode of the first IMD being activated, and the second trigger event that is monitored for (at steps 610 and/or 612) comprises the MRI mode of the first IMD being deactivated. Accordingly, with such embodiments, the first IMD can communication with the second IMD using RF communication during a period of time (e.g., the second period of time) that a patient (in which the first and second IMDs are implanted) is being scanned using an MRI system, thereby enabling the first and second IMDs to continuously synchronously pace the patient even when the MRI system prevents the use of conductive communication.

The MRI mode of the first IMD can be manually or automatically activated and deactivated, depending upon the embodiment and implementation. For example, in certain embodiments, the MRI mode of the first IMD is activated using an external programmer (e.g., 109), or some other types of non-implanted device. In such embodiments, the MRI mode of the first IMD can be deactivated using an external programmer that can be the same as or different than the external programmer that activated the MRI mode. For example, when a patient (within which the first and second IMDs are implanted) visits a radiology clinic, a hospital, or the like, for the purpose of having an MRI scan, a clinician can use an external programmer (e.g., 109) to activate the MRI mode of the IMDs. Then, after the MRI scan has been completed, the clinician can use the external programmer (e.g., 109) to deactivate the MRI mode. It would also be possible for the MRI mode to be deactivated in response to an MRI timeout period expiring. More specifically, an amount of time since the MRI mode was initially activated can be monitored using a timer, or a controller (e.g., 112), to determine whether an MRI timeout period has elapsed. The MRI timeout period can, for example, be in the range of 1 hour to 10 hours, and in a specific example can be 6 hours. The MRI timeout period can be pre-programmed to a default value (e.g., 6 hours), but may be reprogrammed by a clinician. A benefit of having the IMD automatically deactivate the MRI mode, after the MRI time out period expires, is that the IMD will soon transition back to using conductive communication to send messages to the second IMD, even if a clinician forgets to deactivate the MRI mode after the MRI scan has been completed.

In accordance with certain embodiments, the MRI mode of the first IMD is automatically activated in response to a sensor of the first IMD detecting a magnetic field, or a surrogate thereof, that is likely generated by an MRI system. For example, a magnetic field sensor (e.g., 156 in FIG. 2) that is capable of detecting the relatively large static magnetic fields produced by MRI systems can be used to detect a magnetic field that is likely generated by an MRI system, and in response thereto, a controller (e.g., 112) of the first IMD can automatically activate the MRI mode of the first IMD. As was described above, in the discussion of FIG. 2, such a magnetic field sensor can be, e.g., a Hall effect sensor, a GMR sensor, or a reed switch, but is not limited thereto. The MRI mode of the first IMD can then be automatically deactivated in response to the magnetic field sensor (e.g., 156) no longer detecting a magnetic field that is likely generated by an MRI system. It would also be possible for the MRI mode to be deactivated in response to an MRI timeout period expiring. Example details of how the MRI mode may be deactivated in response to an MRI timeout period expiring were described above, and thus, need not be repeated.

Instead of, or in addition to, using a magnetic field sensor (e.g., 156) to detect a magnetic field for the purpose of determining when the LP 102 (or other type of IMD) is likely being exposed to an MRI system, and thus, that a first trigger event is detected, another type of sensor can be used to detect a surrogate of a magnetic field that is likely produced by an MRI system, which in response to be detected, causes an MRI mode of the IMD to be activated. Such a surrogate of a magnetic field that is produced by an MRI system can be a secondary acoustic and/or vibratory effect of an MRI system. More specifically, the accelerometer (e.g., 143 in FIG. 2), or some other sensor configured to detect acceleration, sound and/or vibration of the LP IMD, while not capable of actually detecting the magnetic field from an MRI system, can detect secondary acoustic and/or vibratory effects of an MRI system, which in response to being detected, can cause an MRI mode of the IMD to be automatically activated. The MRI mode can then be automatically deactivated in response to the same sensor (e.g., the accelerometer 143) no longer detecting the surrogate of the magnetic field from an MRI system. It would also be possible for the MRI mode to be deactivated in response to an MRI timeout period expiring.

One or more alternative and/or additional type(s) of trigger events can be monitored for at instances of steps 604 and/or 606, and at instances of steps 610 and/or 612. For example, in certain embodiments, the first trigger event that is monitored for at step 604 and/or 606 comprises the first IMD determining that the second IMD did not successfully receive one or more of the messages, intended for the second IMD, that the first IMD transmitted using conductive communication. There are various different ways in which the first IMD can determine that the second IMD did not successfully receive one or more of the messages, intended for the second IMD, that the first IMD transmitted using conductive communication. In an embodiment, the first IMD can make this determination based on the first IMD not receiving an expected acknowledgement (ACK) message from the second IMD. In another embodiment, the first IMD can make this determination based on the first IMD receiving a message from second IMD that informs the first IMD that the second IMD failed to receive a message that the second IMD expected to receive from the first IMD. This can involve, for example, the second IMD sending to the first IMD a message that includes an indicator (e.g., an error code) in its payload, or header, that indicates to the first IMD that the second IMD failed to receive an expected message from the first IMD. For example, where the first IMD is the aLP 102*a* and the second IMD is the vLP 102*b*, the vLP 102*b* may expect to receive an AS or an AP event type of conductive communication message once every cardia cycle from aLP 102*a*, and if the vLP 102*b* does not receive such a message, the vLP 102*b* can send an error code (or other type of indicator) to the aLP 102*a*, which informs the aLP 102*a* that the vLP 102*b* failed to receive an expected AS or AP event message from the aLP 102*a*. For another example, where the first IMD is the vLP 102*b* and the second IMD is the aLP 102*a*, the aLP 102*a* may expect to receive a VS or an VP event type of conductive communication message once every cardia cycle from vLP 102*b*, and if the aLP 102*a* does not receive such a message, the aLP 102*a* can send an error code (or other type of indicator) to the vLP 102*b*, which informs the vLP 102*b* that the aLP 102*a* failed to receive an expected VS or VP event message from the vLP 102*b*. In certain such embodiments, where messages at instances of steps 608*a* are only transmitted using RF communication (but not using conductive communication), then the second trigger event that is monitored for at instances of steps 610 and/or 612 can be a specified amount of time elapsing since the first IMD transitioned to using RF communication (instead of conductive communication) in response to the first trigger event being detected at an instance of step 604 and/or 606. Other variations are also possible, and within the scope of the embodiments described herein.

Gradient noise from an MRI system is just one example of a type of noise that may adversely affect conductive communication, without adversely affecting RF communication. Accordingly, the first trigger event that is monitored for at instances of steps 604 and/or 606 can more generally be a level of noise (e.g., within the frequency range that is used for performing conductive communication) exceeding a first noise threshold, and the second trigger event that is monitored for at instances of steps 610 and/or 612 can be the level of noise being below a second noise threshold, which can be the same as or different than the first noise threshold. Examples of such other types of noise include, but are not limited to, electromagnetic interference (EMI), or noise from an Electronic Article Surveillance (EAS) gate, a power transformer, a wireless charging device, and/or the like.

In accordance with certain embodiments, the first trigger event that is monitored for at instances of steps 604 and/or 606 can be an arrhythmia being detected or arrhythmia therapy being delivered, and the second trigger event that is monitored for at instances of steps 610 and/or 612 can be the arrhythmia no longer being detected or the arrhythmia therapy being completed. For example, if an LP detects ventricular fibrillation (VF), the LP can turn on its RF communication capability to more quickly and reliably communication with an NV-ICD to instruct the ICD to deliver a defibrillation shock. This may be beneficial because RF communication is typically faster and more reliable than conductive communication, and delivery of a defibrillation shock may adversely affect conductive communication. The first trigger event can be the detection of any type of arrhythmia or arrhythmia therapy, or just specific types of arrhythmias or arrhythmia therapies.

In the embodiments described above with reference to FIG. 6A, at instances of step 608a, one or more messages (intended for the second IMD) is/are transmitted by the first IMD using RF communication, without using conductive communication. A potential downside of such embodiments is that the first IMD may not timely identify a point in time when the first IMD can successfully return to transmitting messages (intended for the second IMD) using more energy efficient conductive communication, without using the less energy efficient RF communication. To overcome this potential downside of such embodiments, in alternative embodiments, after the first trigger event is detected, rather than transitioning from sending messages using conductive communication (without using RF communication), to sending messages using RF communication (without using conductive communication), the first IMD transitions to sending messages using both conductive communication and RF communication. Such alternative embodiments are summarized below with reference to the high level flow diagram of FIG. 6B.

Figure 6B:
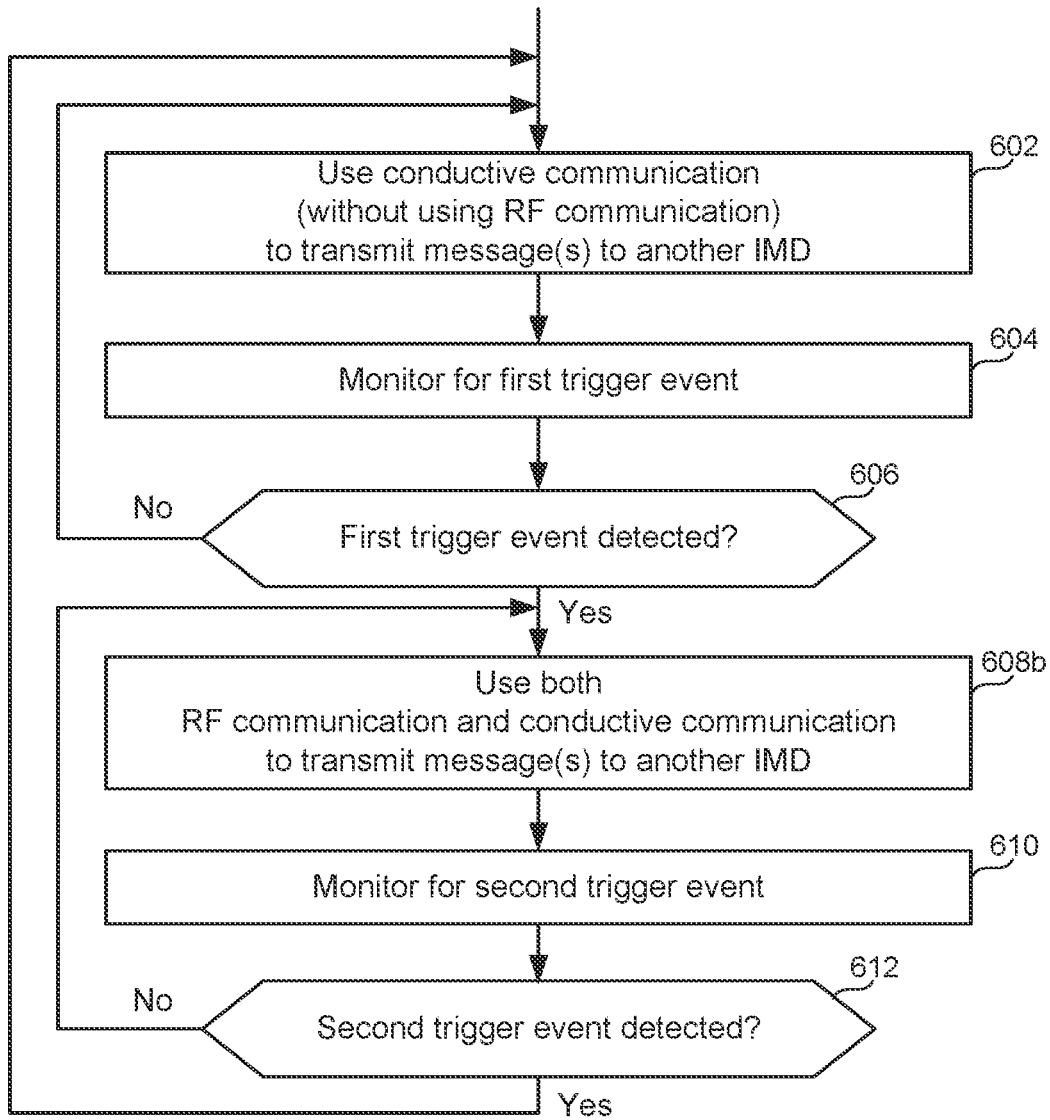
FIG. 6B is a high level flow diagram that is used to summarize methods for improving communication between IMDs, according to other embodiments of the present technology.

A comparison between FIG. 6A and FIG. 6B shows that the only difference between the two flow diagrams is that in FIG. 6B, step 608b is performed in place of the step 608a of FIG. 6A. As shown in FIG. 6B, at step 608b the first IMD uses both RF communication and conductive communication to transmit one or more messages that are intended for the second IMD. In such an embodiment, the first trigger event can be the first IMD determining that the second IMD did not successfully receive one or more of the messages, intended for the second IMD, that the first IMD transmitted using conductive communication. Thereafter, the second trigger event can be the first IMD determining that the second IMD successfully received one or more of the messages, intended for the second IMD, that the first IMD transmitted using conductive communication, thereby enabling the first IMD to stop (at least temporarily) using the less energy efficient RF communication to transmit messages to the second IMD. Example details of how such an embodiment may be implemented are described below with reference to FIG. 7.

Figure 7:
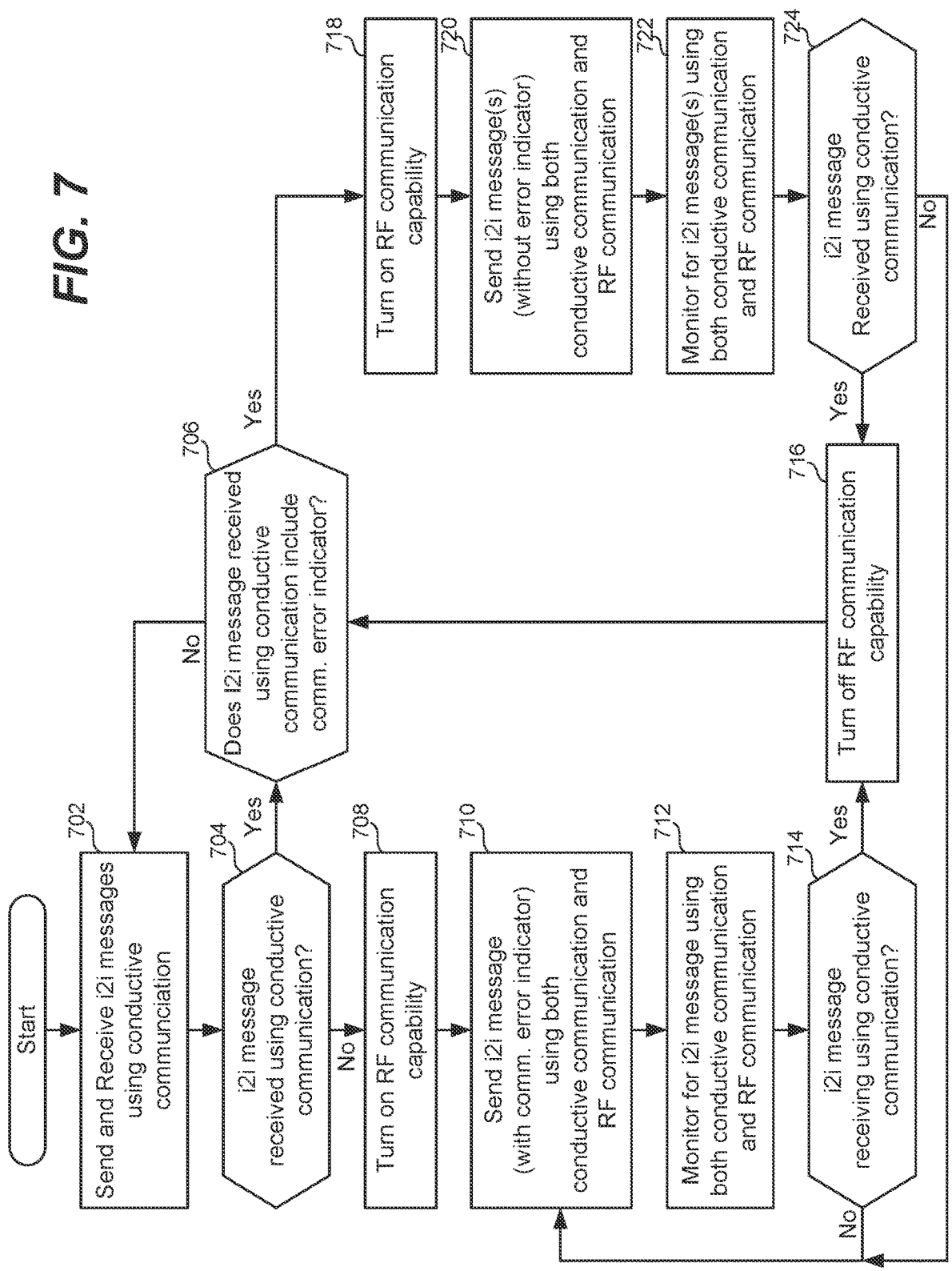
FIG. 7 is a high level flow diagram that is used to summarize methods for improving communication between IMDs, according to specific embodiments of the present technology.

It is noted where one of the embodiments described with reference to FIGS. 6A and 6B is being used to improve the communication between a pair of IMDs, each of the IMDs can separately use such an embodiment to communicate with the other IMD. This also the case where an embodiment described with reference to FIG. 7 is used to improve the communication between a pair of IMDs. The high level flow diagram of FIG. 7 will now be described. In other words, each one of the plurality of IMDs can separately implement the method summarized with reference to FIG. 7 (or FIG. 6A or 6B).

Referring to FIG. 7, step 702 involves an IMD (e.g., a first IMD) sending and receiving i2i messages from another IMD (e.g., a second IMD) using conductive communication. Step 704 involves the IMD determining whether it received an i2i message using conductive communication, from the other IMD, e.g., within a message reception window. If the answer to the determination at step 704 is Yes (i.e., if the IMD received an i2i message from the other IMD using conductive communication), then at step 706 there is a determination of whether the received i2i message included a communication error indicator, which indicated that the other IMD (e.g., the second IMD) did not successfully receive a conductive communication message from the IMD (e.g., the first IMD), e.g., within its own message reception window. If the answer to step 706 is No, then flow returns to step 702. Steps 702, 704, and 706 will continue in a loop so long as the conductive communication between the IMDs is successfully performed.

Returning to step 704, if the answer to the determination at step 704 is No (i.e., if the IMD did not receive an i2i message from the other IMD using conductive communication), then at step 708 an RF communication capability of the IMD is turned on. Then at step 710, the next time the IMD is to send an i2i message to the other IMD, the IMD sends the i2i message to the other IMD using both RF communication and conductive communication, wherein the i2i message includes a communication error indicator that informs the other IMD (e.g., the second IMD) that the IMD (e.g., the first IMD) failed to successfully receive the previous expected i2i message from the other IMD (e.g., the second IMD) using conductive communication. Such an indicator (e.g., an error code) can be included, e.g., in a payload, or a header, of the i2i message that is sent by the IMD to the other IMD using both RF communication and conductive communication. It is noted that the terms send and transmit are often used interchangeably herein, as are the terms sent and transmitted.

At step 712 the IMD monitors for an i2i message from the other IMD using both RF communication and conductive communication. At step 714 there is a determination of whether the IMD received an i2i message from the other IMD using conductive communication. If the answer to the determination at step 714 is No, then flow returns to step 710. The loop that includes steps 710, 712, and 714 will continue until the IMD receives an i2i message from the other IMD using conductive communication. For the sake of this discussion, it is assumed that the IMD is successfully receiving i2i messages from the other IMD using RF communication during a period of time that the loop including 710, 712, and 714 may be repeated. Where an i2i message is received using conductive communication, it can be said that an IMD receives an i2i message over a conductive communication channel. Where an i2i message is received using RF communication, it can be said that the IMD receives an i2i message over an RF communication channel. Because the frequency range that is used for RF communication is above the frequency range that is used for conductive communication, as explained above, it can be said that the frequency of the RF communication channel is above the frequency of the conducive communication channel.

If the answer to the determination at step 714 is Yes, then flow goes to step 716. At step 716 the RF communication capability of the IMD is turned off. After step 716, flow goes to step 706. As noted above, at step 706 there is a determination of whether the received i2i message included a communication error indicator, which indicated that the other IMD (e.g., the second IMD) did not successfully receive a conductive communication message from the IMD (e.g., the first IMD), e.g., within its own message reception window. If the answer to step 706 is No, then flow returns to step 702. However, if the answer to step 706 is Yes, (i.e., if there is an indicator, e.g., an error code) in the i2i message received from the other IMD using conductive communication (which indicated that the other IMD did not successfully receive an expected i2i message using conductive communication), then flow goes to step 718.

At step 718 the RF communication capability of the IMD is turned on. Then at step 720, the next time the IMD is to send an i2i message to the other IMD, the IMD sends the i2i message to the other IMD using both RF communication and conductive communication, wherein the i2i message does not include a communication error indicator that informs the other IMD (e.g., the second IMD) that the IMD (e.g., the first IMD) failed to successfully receive the previous expected i2i message from the other IMD (e.g., the second IMD) using conductive communication.

At step 722 the IMD monitors for an i2i message from the other IMD using both RF communication and conductive communication. At step 724 there is a determination of whether the IMD received an i2i message from the other IMD using conductive communication. If the answer to the determination at step 724 is No, then flow returns to step 710. If the answer to the determination at step 724 is Yes, then flow goes to step 716. At step 716 the RF communication capability of the IMD is turned off. After step 716, flow goes to step 706, which was already explained above.

Since steps 722 and 724 are identical, respectively, to step 712 and 714, it would also be possible to eliminate steps 722 and 724, and that flow goes directly from step 720 to step 712.

In another variation, flow can go directly from step 714 to step 706 (and/or directly from step 724 to step 706), and the RF communication capability can instead be turned off whenever the answer to the determination at step 706 is No. In other words, the flow diagram can be modified such that step 716 is performed between instances of step 706 and 702, whenever the answer to the determination at step 706 is No (i.e., whenever the i2i message that the IMD receives from the other IMD does not include an indicator specifying that the other IMD failed to receive an expected i2i message using conductive communication). Other variations are also possible and within the scope of the embodiments described herein.

As alluded to above, a reason it is better to use conductive communication, than to use RF communication, for sending and receiving i2i messages between IMDs, is that conductive communication is more energy efficient than RF communication, thereby providing for greater IMD longevity. However, there are situations where conductive communication will fail (e.g., during an MRI scan), but RF communication can be successfully used. Accordingly, certain embodiments of the present technology described herein primarily and by default using conductive communication for sending and receiving i2i messages between IMDs, which is energy efficient, and use RF communication as a backup or auxiliary way for sending and receiving i2i messages when needed. A feasibility analysis was performed to determine how much the selective use of RF communication (for sending and receiving i2i messages between IMDs) would affect the longevity of an IMD. Results of the feasibility analysis were that the selective use of RF communication would reduce the battery longevity of an IMD (and thus, the longevity of the IMD) by less than two weeks, compared to if only conductive communication was used for sending messages between the IMDs. Accordingly, where the battery longevity of an IMD is expected to be about 7 years (i.e., about 364 weeks), the selective use of RF communication in an IMD that primarily and by default uses conductive communication, would likely reduce the battery longevity from about 364 weeks to about 362 weeks, which is a reduction in longevity of only about 0.5%. This slight reduction in longevity is believed to be worth the improvement in i2i communication reliability. In other words, it would be worth needing to replace IMDs about 2 weeks early, where the IMDs are expected to last about 7 years, and the IMDs are able to better communicate with one another and provide for synchronous operation (e.g., synchronous pacing) during the slightly shortened lifespan of the IMDs.

While many of the embodiments of the present technology described above have been described as being for use with LP type IMDs, embodiments of the present technology, can also be used with other types of IMDs besides an LP. Accordingly, unless specifically limited to use with an LP, the claims should not be limited to use with LP type IMDs.

Figure 8:
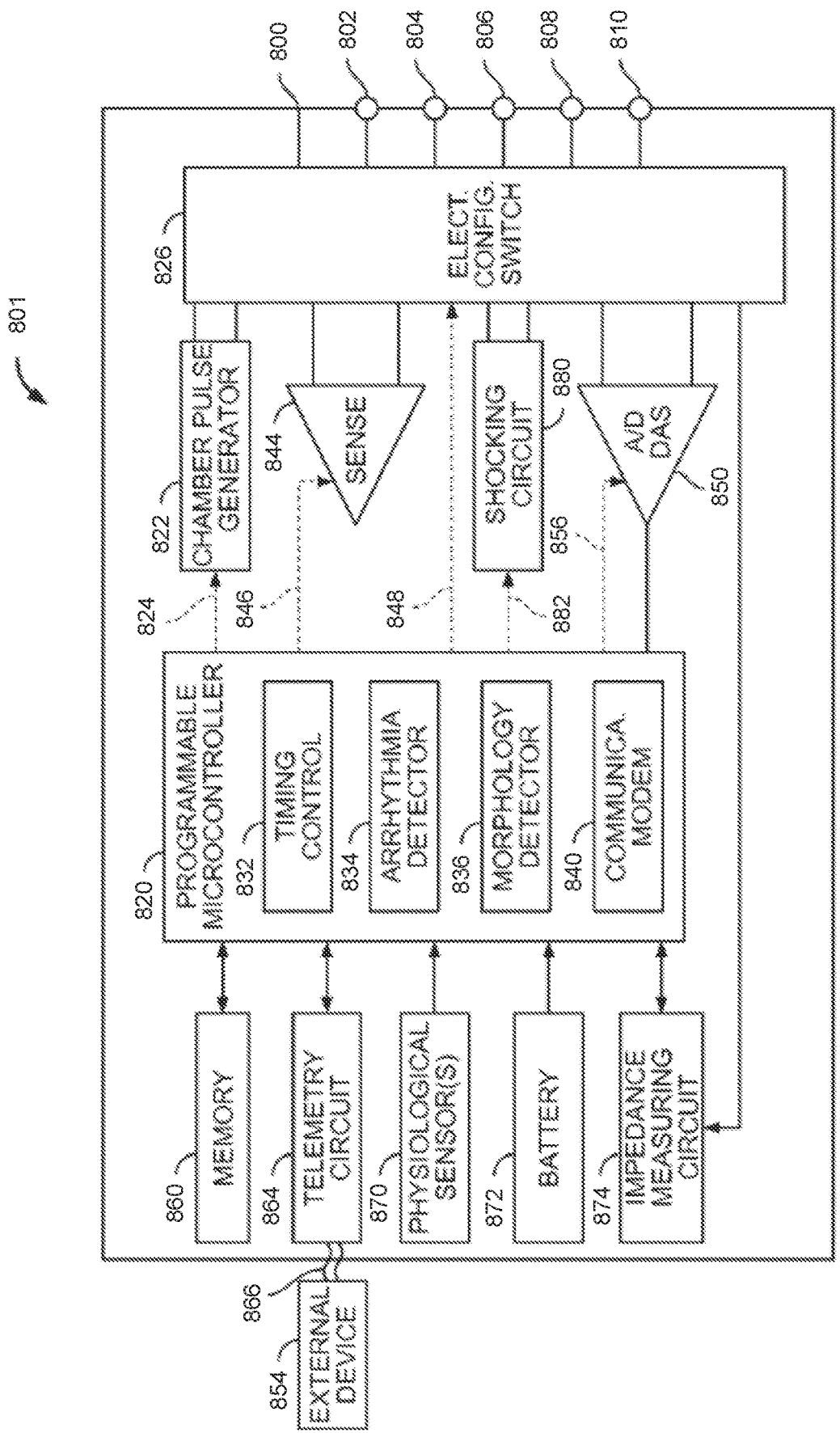
FIG. 8 shows a block diagram of one embodiment of an IMD (e.g., LP or in ICD) that is implanted into the patient as part of the implantable cardiac system in accordance with certain embodiments herein.

FIG. 8 shows a block diagram of one embodiment of an IMD (e.g., an LP or ICD) 801 that is implanted into the patient as part of the implantable cardiac system in accordance with certain embodiments herein. IMD 801 may be implemented as a full-function biventricular pacemaker, equipped with both atrial and ventricular sensing and pacing circuitry for four chamber sensing and stimulation therapy (including both pacing and shock treatment). Optionally, IMD 801 may provide full-function cardiac resynchronization therapy. Alternatively, IMD 801 may be implemented with a reduced set of functions and components. For instance, the IMD may be implemented without ventricular sensing and pacing.

IMD 801 has a housing 800 to hold the electronic/computing components. Housing 800 (which is often referred to as the "can", "case", "encasing", or "case electrode") may be programmably selected to act as the return electrode for certain stimulus modes. Housing 800 may further include a connector (not shown) with a plurality of terminals 802, 804, 806, 808, and 810. The terminals may be connected to electrodes that are located in various locations on housing 800 or elsewhere within and about the heart. IMD 801 includes a programmable microcontroller 820 that controls various operations of IMD 801, including cardiac monitoring and stimulation therapy. Microcontroller 820 includes a microprocessor (or equivalent control circuitry), RAM and/or ROM memory, logic and timing circuitry, state machine circuitry, and I/O circuitry.

IMD 801 further includes a first pulse generator 822 that generates stimulation pulses for delivery by one or more electrodes coupled thereto. Pulse generator 822 is controlled by microcontroller 820 via control signal 824. Pulse generator 822 may be coupled to the select electrode(s) via an electrode configuration switch 826, which includes multiple switches for connecting the desired electrodes to the appropriate I/O circuits, thereby facilitating electrode programmability. Switch 826 is controlled by a control signal 828 from microcontroller 820.

In the embodiment of FIG. 8, a single pulse generator 822 is illustrated. Optionally, the IMD may include multiple pulse generators, similar to pulse generator 822, where each pulse generator is coupled to one or more electrodes and controlled by microcontroller 820 to deliver select stimulus pulse(s) to the corresponding one or more electrodes.

Microcontroller 820 is illustrated as including timing control circuitry 832 to control the timing of the stimulation pulses (e.g., pacing rate, atrio-ventricular (AV) delay, atrial interconduction (A-A) delay, or ventricular interconduction (V-V) delay, etc.). Timing control circuitry 832 may also be used for the timing of refractory periods, blanking intervals, noise detection windows, evoked response windows, alert intervals, marker channel timing, and so on. Microcontroller 820 also has an arrhythmia detector 834 for detecting arrhythmia conditions and a morphology detector 836.

Although not shown, the microcontroller 820 may further include other dedicated circuitry and/or firmware/software components that assist in monitoring various conditions of the patient's heart and managing pacing therapies.

IMD 801 is further equipped with a communication modem (modulator/demodulator) 840 to enable wireless communication with the remote slave pacing unit. Modem 840 may include one or more transmitters and two or more receivers as discussed herein in connection with FIG. 2. In one implementation, modem 840 may use low or high frequency modulation. As one example, modem 840 may transmit i2i messages and other signals through conductive communication between a pair of electrodes and/or using RF communication. Modem 840 may be implemented in hardware as part of microcontroller 820, or as software/firmware instructions programmed into and executed by microcontroller 820. Alternatively, modem 840 may reside separately from the microcontroller as a standalone component. In certain embodiments, the modem 840 includes both a conductive communication transceiver and an RF communication transceiver. While not specifically shown in FIG. 8, such an RF communication transceiver can be coupled to an antenna that enables RF communication signals to be transmitted and received for the purpose of transmitting and receiving messages to and from another IMD.

IMD 801 includes a sensing circuit 844 selectively coupled to one or more electrodes, that perform sensing operations, through switch 826 to detect the presence of cardiac activity in the right chambers of the heart. Sensing circuit 844 may include dedicated sense amplifiers, multiplexed amplifiers, or shared amplifiers. It may further employ one or more low power, precision amplifiers with programmable gain and/or automatic gain control, bandpass filtering, and threshold detection circuit to selectively sense the cardiac signal of interest. The automatic gain control enables the unit to sense low amplitude signal characteristics of atrial fibrillation. Switch 826 determines the sensing polarity of the cardiac signal by selectively closing the appropriate switches. In this way, the clinician may program the sensing polarity independent of the stimulation polarity.

The output of sensing circuit 844 is connected to microcontroller 820 which, in turn, triggers or inhibits the pulse generator 822 in response to the presence or absence of cardiac activity. Sensing circuit 844 receives a control signal 846 from microcontroller 820 for purposes of controlling the gain, threshold, polarization charge removal circuitry (not shown), and the timing of any blocking circuitry (not shown) coupled to the inputs of the sensing circuitry.

In the embodiment of FIG. 8, a single sensing circuit 844 is illustrated. Optionally, the IMD may include multiple sensing circuits, similar to sensing circuit 844, where each sensing circuit is coupled to one or more electrodes and controlled by microcontroller 820 to sense electrical activity detected at the corresponding one or more electrodes. Sensing circuit 844 may operate in a unipolar sensing configuration or in a bipolar sensing configuration.

IMD 801 further includes an analog-to-digital (A/D) data acquisition system (DAS) 850 coupled to one or more electrodes via switch 826 to sample cardiac signals across any pair of desired electrodes. Data acquisition system 850 is configured to acquire intracardiac electrogram signals, convert the raw analog data into digital data, and store the digital data for later processing and/or telemetric transmission to an external device 854 (e.g., a programmer, local transceiver, or a diagnostic system analyzer). Data acquisition system 850 is controlled by a control signal 856 from the microcontroller 820.

Microcontroller 820 is coupled to a memory 860 by a suitable data/address bus. The programmable operating parameters used by microcontroller 820 are stored in memory 860 and used to customize the operation of IMD 801 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart within each respective tier of therapy.

The operating parameters of IMD 801 may be non-invasively programmed into memory 860 through a telemetry circuit 864 in telemetric communication via communication link 866 with external device 854. Telemetry circuit 864 allows intracardiac electrograms and status information relating to the operation of IMD 801 (as contained in microcontroller 820 or memory 860) to be sent to external device 854 through communication link 866.

IMD 801 can further include magnet detection circuitry (not shown), coupled to microcontroller 820, to detect when a magnet is placed over the unit. A magnet may be used by a clinician to perform various test functions of IMD 801 and/or to signal microcontroller 820 that external device 854 is in place to receive or transmit data to microcontroller 820 through telemetry circuits 864.

IMD 801 can further include one or more physiological sensors 870. Such sensors are commonly referred to as "rate-responsive" sensors because they are typically used to adjust pacing stimulation rates according to the exercise state of the patient. However, physiological sensor 870 may further be used to detect changes in cardiac output, changes in the physiological condition of the heart, or diurnal changes in activity (e.g., detecting sleep and wake states). Signals generated by physiological sensors 870 are passed to microcontroller 820 for analysis. Microcontroller 820 responds by adjusting the various pacing parameters (such as rate, AV Delay, V-V Delay, etc.) at which the atrial and ventricular pacing pulses are administered. While shown as being included within IMD 801, physiological sensor(s) 870 may be external to IMD 801, yet still be implanted within or carried by the patient. Examples of physiologic sensors might include sensors that, for example, sense respiration rate, pH of blood, ventricular gradient, activity, position/posture, minute ventilation (MV), and so forth.

A battery 872 provides operating power to all of the components in IMD 801. Battery 872 is capable of operating at low current drains for long periods of time, and is capable of providing high-current pulses (for capacitor charging) when the patient requires a shock pulse (e.g., in excess of 2 A, at voltages above 2 V, for periods of 10 seconds or more). Battery 872 also desirably has a predictable discharge characteristic so that elective replacement time can be detected. As one example, IMD 801 employs lithium/silver vanadium oxide batteries.

IMD 801 further includes an impedance measuring circuit 874, which can be used for many things, including: lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring stroke volume; and detecting the opening of heart valves; and so forth. Impedance measuring circuit 874 is coupled to switch 826 so that any desired electrode may be used. In this embodiment IMD 801 further includes a shocking circuit 880 coupled to microcontroller 820 by a data/address bus 882.

It is to be understood that the subject matter described herein is not limited in its application to the details of construction and the arrangement of components set forth in the description herein or illustrated in the drawings hereof. The subject matter described herein is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Further, it is noted that the term "based on" as used herein, unless stated otherwise, should be interpreted as meaning based at least in part on, meaning there can be one or more additional factors upon which a decision or the like is made. For example, if a decision is based on the results of a comparison, that decision can also be based on one or more other factors in addition to being based on results of the comparison.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the embodiments of the present technology without departing from its scope. While the dimensions, types of materials and coatings described herein are intended to define the parameters of the embodiments of the present technology, they are by no means limiting and are example embodiments. Many other embodiments will be apparent to those of skill in the art upon reviewing the above description. The scope of the embodiments of the present technology should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means—plus-function format and are not intended to be interpreted based on 35 U.S.C. § 112(f), unless and until such claim limitations expressly use the phrase "means for" followed by a statement of function void of further structure.

What is claimed is:

1. A method for use with a system including a first implantable medical device (IMD) and a second IMD that are remotely located relative to one another and are capable of communicating with one another using both conductive communication and radio frequency (RF) communication, the method comprising:
   the first IMD using conductive communication to transmit one or more messages intended for the second IMD, without using RF communication to transmit any messages intended for the second IMD, during a first period of time that a first trigger event is not detected;
   the first IMD detecting the first trigger event, and in response thereto, the first IMD using RF communication to transmit one or more messages intended for the second IMD during a second period of time; and
   the first IMD detecting a second trigger event, and in response thereto, the first IMD using conductive communication to transmit one or more messages intended for the second IMD, without using RF communication to transmit any messages intended for the second IMD, during a third period of time.

2. The method of claim 1, further comprising:
the first IMD also using conductive communication to transmit one or more messages intended for the second IMD during the second period of time, such that during the second period of time both RF communication and conductive communication are used by the first IMD.

3. The method of claim 2, wherein:
the one or more messages intended for the second IMD, that are transmitted by the first IMD using conductive communication during the first period of time, are transmitted within a first frequency range;
the one or more messages intended for the second IMD, that are transmitted by the first IMD using conductive communication during the second period of time, are transmitted within the first frequency range; and
the one or more messages intended for the second IMD, that are transmitted by the first IMD using RF communication during the second period of time, are transmitted within a second frequency range that is above the first frequency range.

4. The method of claim 1, wherein:
the first trigger event comprises a magnetic resonance imaging (MRI) mode of the first IMD being activated; and
the second trigger event comprises the MRI mode of the first IMD being deactivated.

5. The method of claim 4, wherein:
the MRI mode of the first IMD is activated using a non-implanted device; and
the MRI mode of the first IMD is deactivated using a non-implanted device that can be the same as or different than the non-implanted device that activated the MRI mode, or the MRI mode is deactivated in response to an MRI timeout period expiring.

6. The method of claim 4, wherein:
the MRI mode of the first IMD is activated in response to a sensor of the first IMD detecting a magnetic field, or a surrogate thereof, that is likely generated by an MRI system; and
the MRI mode of the first IMD is deactivated in response to the sensor of the first IMD no longer detecting the magnetic field, or the surrogate thereof, that is likely generated by an MRI system, or the MRI mode is deactivated in response to an MRI timeout period expiring.

7. The method of claim 1, wherein:
the first trigger event comprises the first IMD determining that the second IMD did not successfully receive one or more of the messages, intended for the second IMD, that the first IMD transmitted using conductive communication.

8. The method of claim 7, further comprising:
the first IMD also using conductive communication to transmit one or more messages intended for the second IMD during the second period of time; and
the second trigger event comprises the first IMD determining that the second IMD successfully received at least one of the one or more messages, intended for the second IMD, that were transmitted by the first IMD using conductive communication during the second period of time.

9. The method of claim 1, wherein:
the first trigger event comprises a level of noise detected by the first IMD exceeding a first noise threshold; and
the second trigger event comprises the level of noise detected by the first IMD being below a second noise threshold, which can be the same as or different than the first noise threshold.

10. The method of claim 1, wherein:
the first trigger event comprises at least one of an arrhythmia being detected or arrhythmia therapy being delivered; and
the second trigger event comprises at least one of the arrhythmia no longer being detected or the arrhythmia therapy being completed.

11. The method of claim 1, wherein:
one of the first IMD and the second IMD comprises a leadless pacemaker (LP); and
the other one of the first IMD and the second IMD comprises another LP, a non-vascular implantable cardioverter-defibrillator (ICD), or an insertable cardiac monitor (ICM).

12. An implantable medical device (IMD) configured to communicate with another IMD that is remotely located relative to the IMD, the IMD comprising:
at least two electrodes;
a conductive communication transceiver coupled to the at least two electrodes and configured to selectively transmit conductive communication messages that are intended for the other IMD, and configured to receive conductive communication messages from the other IMD;
an antenna;
a radio frequency (RF) communication transceiver coupled to the antenna and configured to selectively transmit RF communication messages that are intended for the other IMD, and configured to receive RF communication messages from the other IMD; and
a controller configured to
control the conductive communication transceiver to transmit one or more conductive communication messages intended for the other IMD during a first period of time that a first trigger event is not detected;
detect the first trigger event, and in response thereto, control the RF communication transceiver to transmit one or more RF communication messages intended for the other IMD during a second period of time; and
detect a second trigger event, and in response thereto, control the conductive communication transceiver to transmit one or more conductive communication messages intended for the other IMD during a third period of time;
wherein during the first period of time and the third period of time the RF communication transceiver is not used to transmit any RF communication messages intended for the other IMD.

13. The IMD of claim 12, wherein:
the conductive communication transceiver is configured to transmit and receive messages within a first frequency range; and
the RF communication transceiver is configured to transmit and receive messages within a second frequency range that is above the first frequency range.

14. The IMD of claim 12, wherein:
during the first period of time the RF communication transceiver is disabled, and the conductive communication transceiver is enabled and used for both transmitting and receiving one or more messages using conductive communication.

15. The IMD of claim 14, wherein:
during the second period of time both the RF communication transceiver and the conductive communication transceiver are enabled by the controller; and
the controller is further configured to control the conductive communication transceiver to continue to use conductive communication to transmit one or more messages intended for the other IMD during the second period of time, such that during the second period of time both the RF communication transceiver and the conductive communication transceiver are used by the IMD to send messages to and receive messages from the other IMD.

16. The IMD of claim 15, further comprising a battery that provides power to the controller, wherein the battery also provides power to each of the conductive communication transceiver and the RF communication transceiver when they are enabled, and wherein the RF communication transceiver draws substantially no power from the battery when the RF communication transceiver is disabled.

17. The IMD of claim 15, wherein:
the first trigger event comprises the controller determining that the other IMD did not successfully receive one or more of the messages, intended for the other IMD, that were transmitted by the conductive communication transceiver.

18. The IMD of claim 17, wherein:
the second trigger event comprises the controller determining that the other IMD successfully received at least one of one or more messages, intended for the other IMD, that were transmitted by the conductive communication transceiver during the second period of time.

19. The IMD of claim 12, wherein:
the first trigger event comprises a magnetic resonance imaging (MRI) mode of the IMD being activated; and
the second trigger event comprises the MRI mode of the IMD being deactivated.

20. The IMD of claim 19, wherein:
the MRI mode of the IMD can be selectively activated and deactivated by a non-implanted device.

21. The IMD of claim 19, further comprising:
a sensor configured to detect a magnetic field, or a surrogate thereof, that is likely generated by an MRI system;
wherein the controller is configured to activate the MRI mode in response to the sensor detecting the magnetic field, or the surrogate thereof, that is likely generated by an MRI system; and
wherein the controller is configured to deactivate the MRI mode in response to the sensor no longer detecting the magnetic field, or the surrogate thereof, that is likely generated by an MRI system, or the controller is configured to deactivate the MRI mode in response to an MRI timeout period expiring.

22. The IMD of claim 12, wherein:
the first trigger event comprises a level of noise detected by the IMD exceeding a first noise threshold; and
the second trigger event comprises the level of noise detected by the IMD being below a second noise threshold, which can be the same as or different than the first noise threshold.

23. The IMD of claim 12, wherein:
the first trigger event comprises at least one of an arrhythmia being detected or arrhythmia therapy being delivered by the IMD or the other IMD; and
the second trigger event comprises at least one of the arrhythmia no longer being detected or the arrhythmia therapy being completed.

24. The IMD of claim 12, wherein the IMD comprises one of a leadless pacemaker (LP), a non-vascular implantable cardioverter-defibrillator (ICD), or an insertable cardiac monitor (ICM).

25. A system comprising:
a first implantable medical device (IMD) and a second IMD that are configured to be implanted at different locations within a patient;
wherein each IMD, of the first and the second IMDs, includes a conductive communication transceiver and an RF communication transceiver, the conductive communication transceiver configured to transmit and receive implant-to-implant (i2i) messages using conductive communication, the RF communication transceiver configured to transmit and receive i2i messages using RF communication while the RF communication transceiver is enabled; and
wherein each IMD, of the first and the second IMDs, is configured to
use the conductive communication transceiver of the IMD without using the RF communication transceiver of the IMD to send and receive i2i messages during a period of time that a first trigger event is not detected; and
use both the conductive communication transceiver and the RF communication transceiver of the IMD to send and receive i2i messages during a further period of time, in response to the first trigger event being detected.

26. The system of claim 25, wherein each IMD, of the first and second IMDs, is configured to transition back to using the conductive communication transceiver of the IMD without using the RF communication transceiver of the IMD to send and receive i2i messages, in response to a second trigger event being detected.

27. The system of claim 26, wherein:
the first trigger event comprises a level of noise detected by the first IMD exceeding a first noise threshold; and
the second trigger event comprises the level of noise detected by the first IMD being below a second noise threshold, which can be the same as or different than the first noise threshold.

28. The system of claim 26, wherein:
the first trigger event comprises at least one of an arrhythmia being detected or arrhythmia therapy being delivered by the first IMD or the second IMD; and
the second trigger event comprises at least one of the arrhythmia no longer being detected or the arrhythmia therapy being completed.

29. The system of claim 26, wherein:
the conductive communication transceiver, of each of the first and second IMDs, is configured to transmit and receive i2i messages using conductive communication within a first frequency range,
the RF communication transceiver, of each of the first and second IMDs, is configured to transmit and receive i2i messages using RF communication within a second frequency range that is above the first frequency range.

* * * * *